US008855786B2

(12) United States Patent
Derbas et al.

(10) Patent No.: US 8,855,786 B2
(45) Date of Patent: Oct. 7, 2014

(54) SYSTEM AND METHOD FOR WIRELESS POWER TRANSFER IN IMPLANTABLE MEDICAL DEVICES

(75) Inventors: Justin R. Derbas, Orland Park, IL (US); Vinit Singh, Austin, TX (US)

(73) Assignee: Nucurrent, Inc., Chicago, IL (US)

( * ) Notice: Subject to any disclaimer, the term of this patent is extended or adjusted under 35 U.S.C. 154(b) by 0 days.

(21) Appl. No.: 13/255,659

(22) PCT Filed: Mar. 9, 2010

(86) PCT No.: PCT/US2010/000714
§ 371 (c)(1),
(2), (4) Date: Nov. 22, 2011

(87) PCT Pub. No.: WO2010/104569
PCT Pub. Date: Sep. 16, 2010

(65) Prior Publication Data
US 2012/0095531 A1 Apr. 19, 2012

Related U.S. Application Data

(60) Provisional application No. 61/158,688, filed on Mar. 9, 2009.

(51) Int. Cl.
*A61N 1/00* (2006.01)
(52) U.S. Cl.
USPC ............................................. 607/68; 336/198
(58) Field of Classification Search
USPC ............................................. 607/68; 336/198
See application file for complete search history.

(56) References Cited

U.S. PATENT DOCUMENTS

| | | | |
|---|---|---|---|
| 2,911,605 A | 11/1959 | Wales, Jr. | |
| 3,484,731 A | 12/1969 | Rich | |
| 4,328,531 A | 5/1982 | Nagashima et al. | |
| 4,494,100 A | 1/1985 | Stengel et al. | |
| 4,959,631 A | 9/1990 | Hasegawa et al. | |
| 4,996,165 A | 2/1991 | Chang et al. | |
| 5,237,165 A | 8/1993 | Tingley, III | |
| 5,604,352 A | 2/1997 | Schuetz | |
| 5,748,464 A | 5/1998 | Schuetz | |
| 5,777,538 A | 7/1998 | Schuetz | |
| 5,838,154 A | 11/1998 | Morikawa et al. | |
| 5,883,392 A | 3/1999 | Schuetz | |
| 6,503,831 B2 | 1/2003 | Speakman | |
| 6,809,688 B2 | 10/2004 | Yamada | |
| 6,924,230 B2 | 8/2005 | Sun et al. | |
| 7,713,762 B2 | 5/2010 | Lee et al. | |
| 7,952,365 B2 | 5/2011 | Narita et al. | |
| 8,056,819 B2 | 11/2011 | Rowell et al. | |
| 2002/0105080 A1 | 8/2002 | Speakman | |
| 2003/0119677 A1 | 6/2003 | Qiyan et al. | |
| 2004/0000974 A1* | 1/2004 | Odenaal et al. | ............ 333/219 |
| 2007/0023424 A1* | 2/2007 | Weber | ............ 219/635 |
| 2008/0211320 A1* | 9/2008 | Cook et al. | ............ 307/149 |
| 2009/0015266 A1 | 1/2009 | Narita et al. | |
| 2009/0152542 A1 | 6/2009 | Lee et al. | |

(Continued)

*Primary Examiner* — Christopher D Koharski
*Assistant Examiner* — Michael Carey
(74) *Attorney, Agent, or Firm* — McDermott, Will & Emery LLP

(57) ABSTRACT

A resonator is provided for use in a system for energy transfer between a first device and a second device. The resonator includes a coil having multiple layers, each layer including inductive and insulative layers. The thickness of a conductor layer may be relative to the skin depth of the conductor.

5 Claims, 20 Drawing Sheets

(56) References Cited

U.S. PATENT DOCUMENTS

| | | |
|---|---|---|
| 2009/0261936 A1 | 10/2009 | Widjaja et al. |
| 2011/0248891 A1 | 10/2011 | Han et al. |
| 2012/0235500 A1* | 9/2012 | Ganem et al. ............... 307/104 |
| 2012/0235634 A1 | 9/2012 | Hall et al. |

* cited by examiner

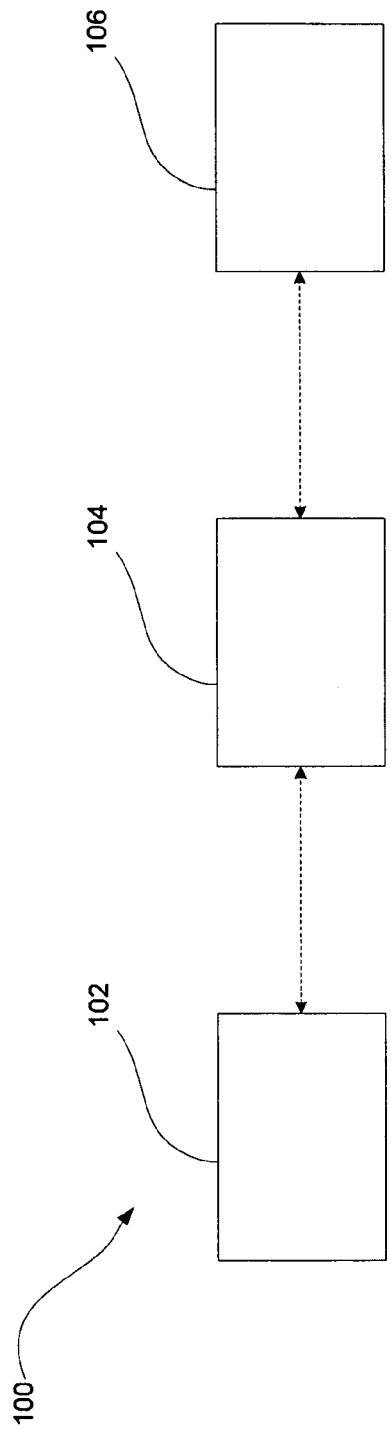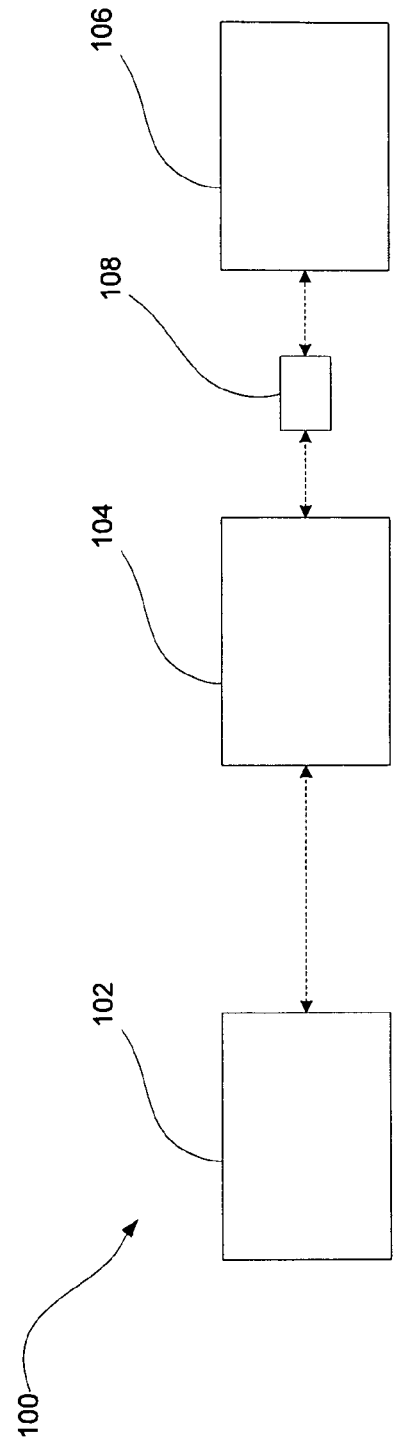

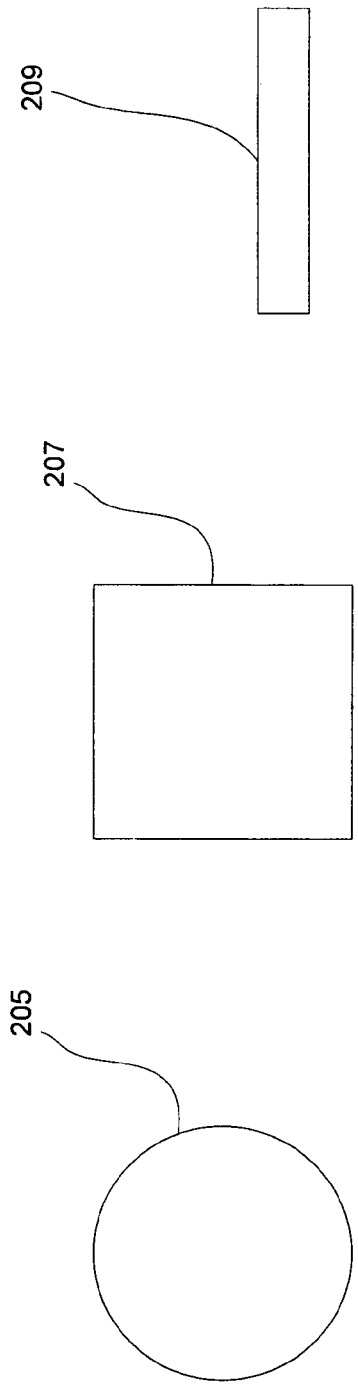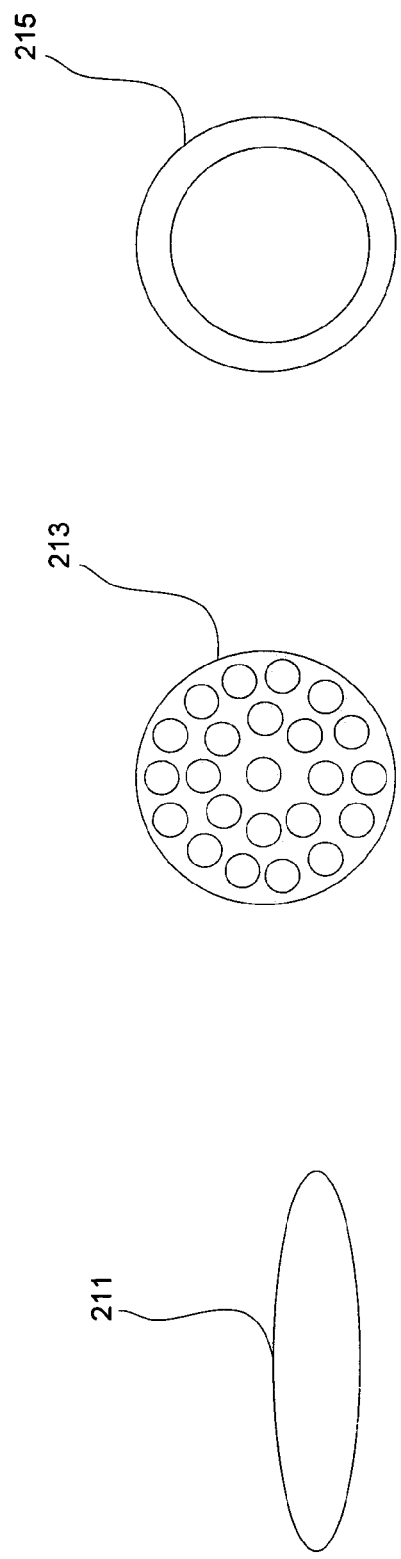
FIG. 13A  FIG. 13B  FIG. 13C  FIG. 13D  FIG. 13E  FIG. 13F

SYSTEM AND METHOD FOR WIRELESS POWER TRANSFER IN IMPLANTABLE MEDICAL DEVICES

CROSS-REFERENCE TO RELATED APPLICATIONS

This Application claims the priority of U.S. Provisional Application No. 61/158,688 filed Mar. 9, 2009.

TECHNICAL FIELD

The present subject matter relates to a system and method for energy transfer between two or more devices, and more specifically, to a system and method for the transfer of power and/or data between two or more devices in near-field communications.

BACKGROUND

In recent years, the use of wireless energy transfer or wireless power transmission has been used to transfer electrical energy from a power transmitter (such as a source) to a receiver without the use of interconnecting wires. Wireless energy transfer is useful in cases where instantaneous or continuous energy transfer is needed where interconnecting wires are inconvenient or hazardous. Typically, wireless energy transfer involves the use of antennas which are used to transmit and/or receive power and data using time-varying currents, such as alternating currents. Such systems are generally referred to as inductively coupled systems.

The efficiency of energy transfer between two devices in an inductively coupled system is based on the quality factor of the antenna in transmitter ($Q_1$), the quality factor of the antenna in the receiver ($Q_2$), and the coupling coefficient between the two antennas ($\kappa$). The efficiency of the energy transfer varies according to the following relationship:

$$\text{eff} \propto \kappa^2 \cdot Q_1 Q_2$$

The quality factor represents the rate of energy loss relative to the stored energy of the antenna. A higher quality factor indicates a lower rate of energy loss relative to the stored energy of the antenna. Conversely, a lower quality factor indicates a higher rate of energy loss relative to the stored energy of the antenna. The coupling coefficient expresses the degree of coupling that exists between two antennas. The value of the coupling coefficient may be based on the proximity of the antennas, the orientation of each antenna relative to the other antenna, and the environment in which the antennas are located. A higher coupling coefficient may be achieved by placing the antennas closer to one another, by orientating each antenna such that electromagnetic fields generated by the antenna are aligned, or removing environmental elements that reduce the strength of the generated electromagnetic fields.

Although the quality factor may increase the efficiency of an inductively coupled system, the quality factor inversely affects the bandwidth that is available to transmit data. Specifically, the bandwidth available to transmit data (BW) is inversely proportional to the quality factor of an antenna and varies according to the following relationship:

$$BW \propto \frac{1}{Q}$$

As a result, a higher quality factor reduces the available bandwidth for data transmission. Given the mathematical relationship between the bandwidth and quality factor, data-intensive systems that require significant bandwidth will require that the quality factors of the transmitting and receiving antennas be decreased. The low quality factor of the antennas in these systems requires a high coupling coefficient in order to increase the efficiency of energy transfer between the transmitter and the receiver in the system. However, often times, it may not be possible to increase the coupling coefficient due to the various environmental constraints.

Recently, implantable tissue stimulation systems have been developed to provide electrical stimulation for the treatment and management of chronic intractable pain, heart arrhythmia, and other medical conditions in which stimulation may be beneficial. Generally, these systems include an implantable controller device and at least one stimulating electrode for providing electrical stimulation to tissue. The implantable controller device (such as an implantable pulse generator) controls the stimulation that is provided to the tissue. The implantable controller device may control the stimulation by providing continuous stimulation control signals to the stimulating electrodes that control the pulse amplitude, pulse width and frequency, and pulse pattern applied by the stimulating electrode. Wire leads originate from the implantable controller device and terminate in stimulating electrodes at the stimulation site. One disadvantage of current tissue stimulation systems is the formation of scar tissue around the lead wires leading to the breakage and/or migration of the lead wires due to stress and strain caused by body movement. An improvement over these existing systems would be to remove the wires and design a system in which the implantable controller device could wirelessly provide power and stimulation control signals to the stimulating electrodes.

Currently available implantable tissue simulation systems also require high-data transfer rates because the implantable controller device controls the stimulation by providing continuous signals to the stimulating electrodes. As noted above, in wireless communications, data intensive systems require substantial bandwidth. In designing such systems, the quality factors of the transmitting and receiving antennas must be reduced in order to achieve the necessary bandwidth required for data transmission. Thus, in order to achieve high efficiency systems with a low quality factor; it is necessary to have a high coupling coefficient between the transmitter and the receiver in the system. However, it may not be possible to achieve a high coupling coefficient in certain environments.

Thus, there currently exists a need for an improved system and method for energy transfer between two more or more devices in a system via high quality factor resonant inductive coupling.

SUMMARY

The teachings herein alleviate one or more of the above noted problems. One aspect of the present teaching is a system for energy transfer between a transmitting unit and a receiving unit. The system includes a transmitting unit, a receiving unit, and a load. The receiving unit may be in the near-field of the transmitting unit.

The transmitting unit may include a transmitting antenna circuit having a first resonant frequency and a high quality factor. The transmitting antenna circuit may generate an electromagnetic field for wireless transfer of power and periodically generate a modulated time-varying signal for the transfer of data. The transmitting antenna circuit may have a quality factor greater than 100. Preferably, the quality factor is greater than 350. Most preferably, the quality factor is greater than 600. It is understood that traditional inductively coupled systems utilize antennas with a quality factor around 30.

The receiving unit is wirelessly coupled to the transmitting unit. The receiving unit may include a receiving antenna circuit having a second resonant frequency and a high quality factor. The second resonant frequency may be substantially equal to the first resonant frequency. The receiving antenna circuit may detect the electromagnetic field generated by the transmitting unit, generate an induced electric current and detect the modulated time-varying signal periodically generated by the transmitting unit. The receiving antenna circuit may have a quality factor greater than 100. The receiving unit may also include a pickup antenna circuit inductively coupled to the receiving antenna circuit.

The load is coupled to the receiving unit wherein the induced electric current powers the load. The load may include a demodulation circuit for demodulating the time-varying signal received by the receiving unit.

The system may also include one or more repeaters for detecting the electromagnetic field generated by the transmitting unit. The one or more repeaters may generate an induced electric current and may include repeater antenna circuit to produce a second electromagnetic field based on the induced current. The second electromagnetic field may be used to generate an induced current in a receiving unit.

Another aspect of the present teaching is a system for providing electrical stimulation to human tissue. The system may include a first implantable device and a second implantable device.

The first implantable device may include a first resonator having a first resonant frequency and a high quality factor. The first resonator may generate an electromagnetic field for wireless transfer of power and periodically generate a modulated time-varying signal comprising of at least one set of control information. The first resonator may have a quality factor greater than 100. The control information may include at least one of an identity of at least one stimulating electrode, a pulse amplitude to apply at the at least one stimulating electrode, a pulse width and frequency of a stimulation to be applied, and a pulse pattern to apply at the at least one selected electrode.

The first implantable device may include a first circuit for generating a first electric current wherein the first electric current is used to generate the electromagnetic field generated by the first resonator. The first circuit may include a first processor, a battery component, an oscillator and amplifier component, and a feed component. The first processor may provide parameters to generate the first electric current. The battery component may generate a second electric current. The oscillator and amplifier component may be coupled to the battery component and the first processor and may receive the second electric current from the battery component and convert the second electric current into a third electric current based on parameters received from the first processor. The feed component may be coupled to the oscillator and amplifier component, the first processor and the first resonator, and may receive the third electric current from the oscillator and amplifier component and generate the first electric current based on for parameters received from the first processor.

The second implantable device may have a second resonator inductively coupled to the first resonator. The second resonator may have a second resonant frequency and a high quality factor. The second resonator may have a quality factor greater than 100. The second resonator may detect the electromagnetic field generated by the first resonator, generate an induced electric current and detect the modulated time-varying signal comprising the at least one set of control information periodically generated by the first resonator. The second implantable device may include a stimulus driver and at least one simulating electrode for providing selected stimulation to human tissue based on the induced current generated by the second resonator. The second implantable device may include a second processor coupled to a memory location. The second processor may demodulate the time-varying signal received by the second resonator to extract the control information and storing the control information in the memory location.

The second implantable device may include a second circuit for generating a stimulation current based on the induced current generated by the second resonator. The stimulation current is used to provide stimulation to human tissue. The second circuit may include the second processor, a rectifier and filter component, and a regulator component. The second processor may be coupled to the second resonator and the stimulation driver and have a memory location having at least one set of control information. The at least one set of control information may be selected for providing selected stimulation to human tissue. The rectifier and filter component may be coupled to the second resonator and second processor, and may receive the induced current from the second resonator and generate a fourth electric current based on the selected control information. The regulator component may be coupled to the rectifier and filter component and receive the fourth electric current from the rectifier and filter component and generate one or more constant voltages based on the selected control information. One constant voltage may be supplied to the stimulus driver. Other constant voltages may be supplied to other components within the second implantable device, such as, for example, the second processor.

The second implantable device may also include a feedback circuit for detecting sensory information and may periodically generate a modulated time-varying signal comprising at least a portion of the sensory information.

The system may also include an external device coupled to the first implantable device. The external device may include an external circuit for transmitting power and control information to the first implantable device.

Yet another aspect of the present teachings is a method for providing electrical stimulation to human tissue in a system having a first implantable device having a first resonator having a first resonant frequency and a high quality factor and a second implantable device having a second resonator inductively coupled to the first resonator wherein the second resonator having a second resonant frequency and a high quality factor. The method may comprise the steps of detecting an electromagnetic field generated by the first resonator; generating an induced current, wherein the induced current is an alternating current; generating a stimulation current based on the induced current; and, applying the stimulation current to human tissue. The stimulation current may be generated based on at least one of a pulse amplitude, a pulse width and frequency, and a pulse pattern. The method may also include the steps of detecting a modulated time-varying signal generated by the first resonator, wherein the signal comprising at least one set of control information periodically; demodulating the time-varying signal to extract the control information; and storing the at least one set of control information in the memory location in the second implantable device. The method may also include the steps of detecting sensory information; and generating a modulated time-varying signal comprising at least a portion of the sensory information.

Another aspect of the present teachings is a resonator for use in a system for energy transfer between a first device and a second device. The resonator may include a coil having an operating frequency, the coil having at least one turn wherein the at least one turn has a plurality of layers further wherein each layer in the plurality of layers is electrically connected to the other layers in the plurality of layers. Each layer may include an insulator for insulating the layer from the other layers. Each layer in the plurality of layers may be electrically connected to the other layers using at least one via. The lay may include a thickness substantially equal to twice the skin-depth at the operating frequency.

Additional advantages and novel features will be set forth in part in the description which follows, and in part will become apparent to those skilled in the art upon examination of the following and the accompanying drawings or may be learned by production or operation of the examples. The advantages of the present teachings may be realized and attained by practice or use of various aspects of the methodologies, instrumentalities and combinations set forth in the detailed examples discussed below.

BRIEF DESCRIPTION OF THE DRAWINGS

The drawing figures depict one or more implementations in accord with the present teachings, by way of example only, not by way of limitation. In the figures, like reference numerals refer to the same or similar elements.

FIG. 2A illustrates an example of a high-level block diagram of a system for stimulating human tissue;

FIG. 2B illustrates an example of a high-level block diagram of a system for stimulating human tissue;

FIGS. 13A-13F illustrate examples of cross-sections of wires that may be used in the design of a resonant component;

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The various technologies described herein generally relate to a system and method for energy transfer between two or more devices via high quality factor (Q) resonant inductive coupling, and more specifically, to a system and method for the transfer of power and/or data between two or more devices in near-field communications via high-Q resonant inductive coupling.

Figure 1A:
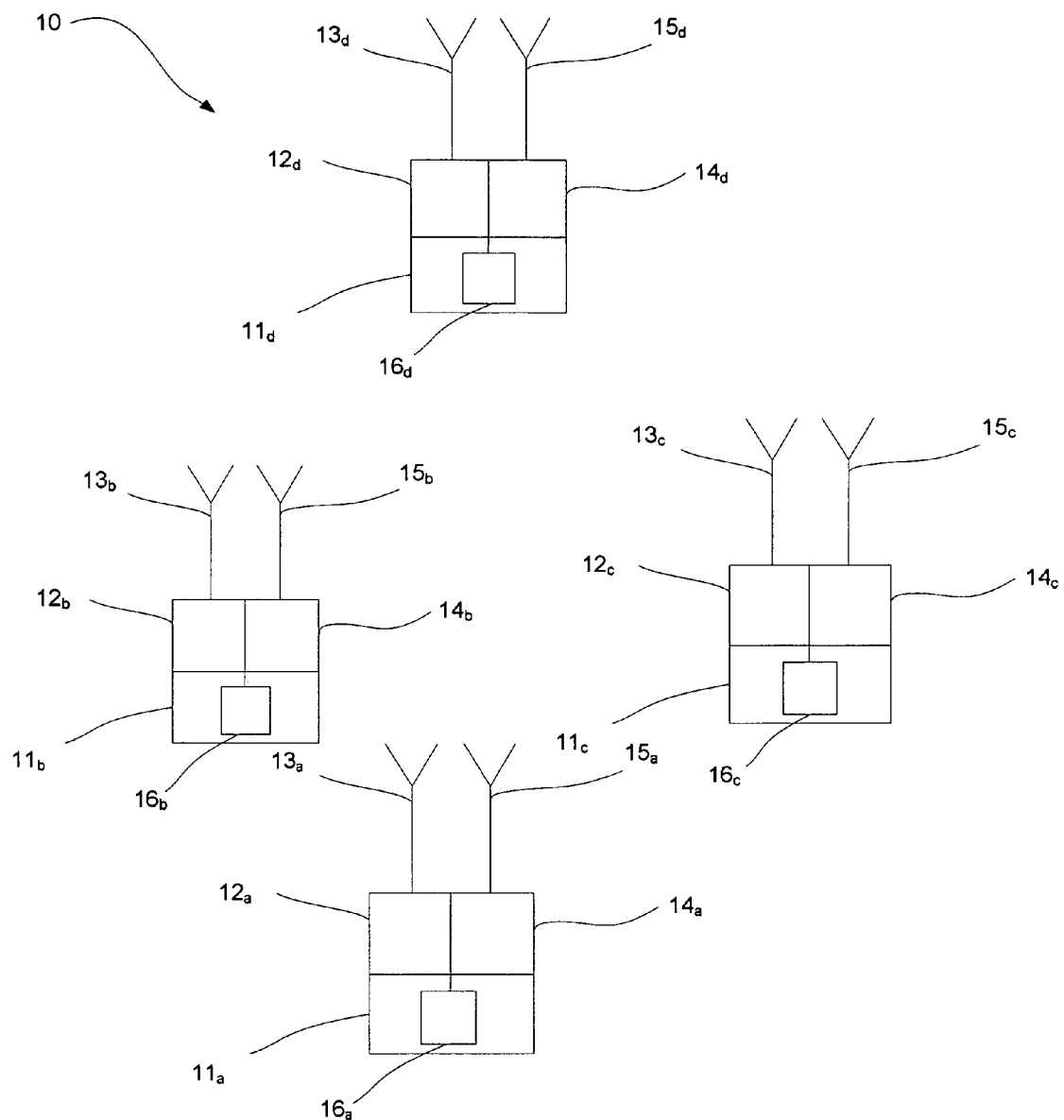
FIG. 1A illustrates an example of a high-level block diagram of a near-field energy network.

FIG. 1A illustrates a high-level block diagram of a near-field energy network 10. The network 10 includes a plurality of devices $11_{a-d}$ (generally referred to as device 11). Each device 11 may include a transceiver. The transceiver may include a transmitting unit $12_{a-d}$ and a receiving unit $14_{a-d}$ for wireless communications. Although each transceiver may include a transmitting unit 12 and a receiving unit 14, it is understood that the transceiver may comprise only a transmitting unit 12 or only a receiving unit 14. Further, it is understood that the transmitting unit 12 and the receiving unit 14 in the transceiver may share certain or all circuit elements or may have separate and distinct circuit elements. Further, as will be described in greater detail herein, the transmitting unit 12 and/or receiving unit 14 may be coupled to a load 16. The load 16 may comprise of components within the device 11, outside the device 11, or a combination of components within and outside the device 11.

Each transmitting unit 12 includes a transmitting antenna 13. The transmitting antenna 13 has a resonant frequency $\omega_s$ and preferably has minimal resistive and radiative losses. The load 16 may include driver circuitry to generate signals to drive the transmitting antenna 13. Based on the received signals, the transmitting antenna 13 may produce a near-field in all directions (omni-directional) or may produce a near-field targeted towards a specific direction (directional). The targeted near-field may be produced through shielding, such as by ferrite materials. Of course, it is understood to those skilled in the art that other materials may be used to provide targeted near-fields.

Each receiving unit 14 includes a receiving antenna 15. A single antenna may be used for both the receiving antenna 15 and the transmitting antenna 13 or a separate antenna may be used for the receiving antenna 15 and the transmitting antenna 13. Each antenna 13, 15 has a resonant frequency (referred to as $\omega_a$-$\omega_d$). If separate transmitting and receiving antenna are used, it is preferred that the resonant frequency of the receiving antenna 15 is equal to the resonant frequency of the transmitting antenna 13.

When a receiving unit 14 of one device 11 (e.g., receiving unit $14_b$) is placed in the near-field of the transmitting unit 12 of another device 11 (e.g., transmitting unit $12_a$), an electromagnetic field generated by the transmitting unit $12_a$ will interact with the receiving unit $14_b$. When the resonant frequency $\omega_a$ of receiving unit $14_a$ is the same as the resonant frequency $\omega_s$ of transmitting unit $12_a$, the electromagnetic field generated by the transmitting unit $12_a$ will induce an alternating current within receiving unit $14_a$. The induced alternating current may be used to power the load $16_b$ connected to receiving unit $14_b$ or transmit data from the transmitting unit $12_a$ to receiving unit $14_b$. The alternating current may also be used to charge a power storage device, such as a battery, in the load $16_b$. Any number of receiving units 14 having resonant frequencies equal to $\omega_s$ may be added to the near field and draw energy from transmitting unit 12 if the resonance frequency of the transmitting antenna 13 is not significantly altered due to the loading effect on the receiving units 14. Preferably, the transmitting antenna 13 and receiving antenna 15 are designed to have high quality factors to achieve efficient energy transfer between devices 11. The transmitting antenna 13 and receiving antenna 15 may have quality factors greater than 100. The quality factors may also be greater than 350. Preferably, the quality factors are greater than 600. It is understood that traditional inductively coupled systems utilize antennas with a quality factor around 30.

In addition to transferring power, the energy transfer may be used to transfer data from a transmitting unit 12 in one device (e.g., transmitting unit $12_a$) to a receiving unit 14 in another device (e.g., receiving unit $14_b$). As will be described herein, the receiving units 14 may be designed to receive data, transmit data, or receive and transmit data. If the receiving unit 14 is designed to receive and transmit data, the receiving unit 14 may have a shared antenna 13 for receiving and transmitting, or separate dedicated antennas 13, 15 for transmitting and receiving data. The receiving units 14 may also be designed transfer data, transfer power, or transfer data and power. If the receiving unit 14 is designed to transfer power and data, each receiving unit 14 may use any combination of sending data, receiving data, sending power, and/or receiving power. It is also contemplated that each receiving unit 14 may use a shared antenna for data and power transfer, or each receiving unit 14 may have a separate dedicated antennas for power transfer and data transfer.

When a receiving unit 14 (e.g., receiving unit $14_b$) is placed within the near-field of the transmitting unit 12 (e.g., transmitting unit $12_a$) and both the receiving unit $14_b$ and the transmitting unit $12_a$ resonate at the same frequency and have antennas having high quality factors, energy will efficiently transfer from the transmitting unit $12_a$ to the receiving unit $14_b$. It is understood that if additional receiving units $14_c$-$14_d$ are placed in the near-field, the additional receiving units $14_c$-$14_d$ will also resonate at the same frequency and draw energy from transmitting unit $12_a$ in the form of an induced alternating current. The receiving units $14_a$-$14_d$ may include a transducer which may use the induced alternating current to store energy in a power storage device, such as battery or capacitor. Alternatively, the transducer may use induced alternating current to directly power electronic components within the receiving unit 14.

Figure 1B:
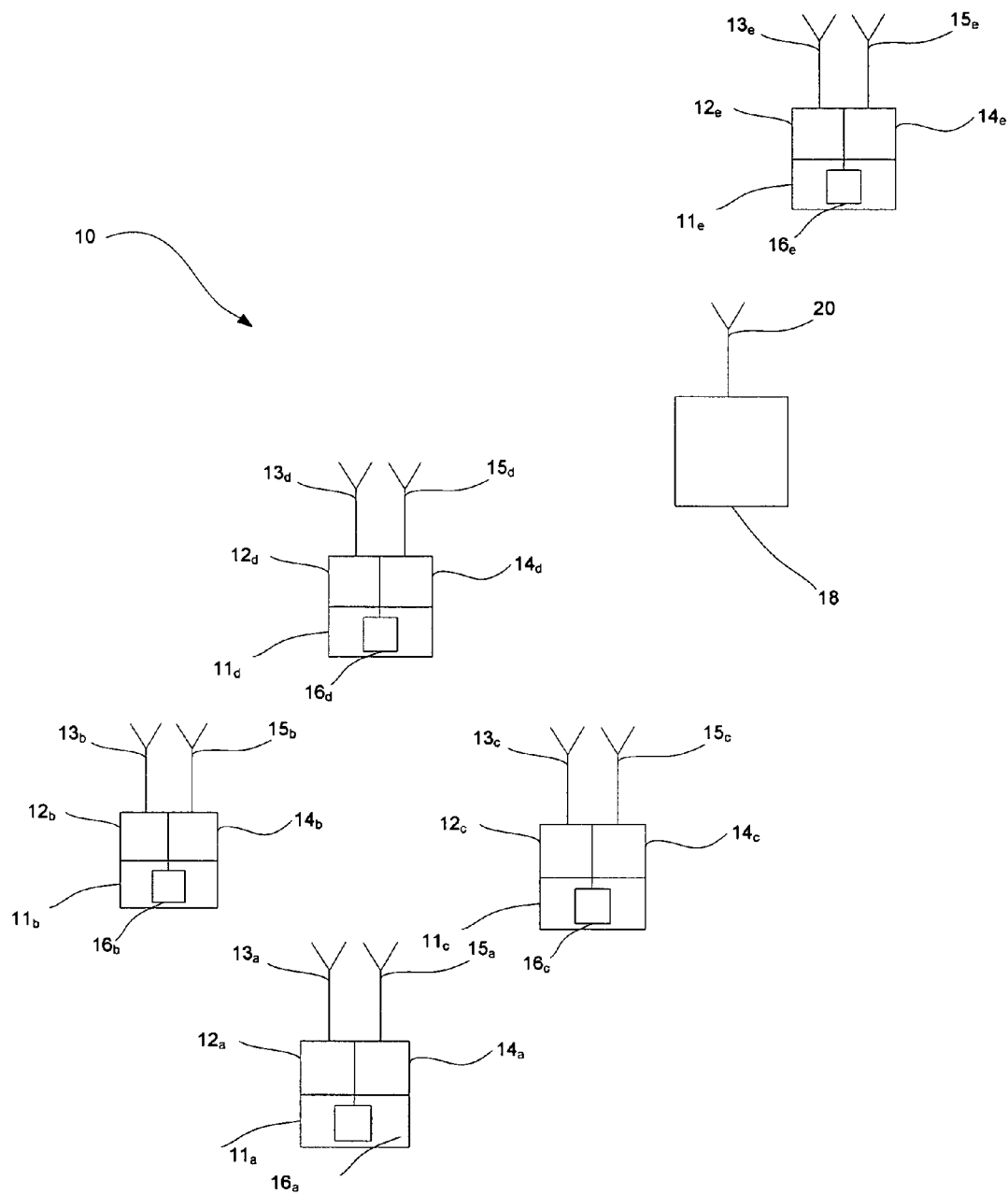
FIG. 1B illustrates an example of a high-level block diagram of a near-field energy network.

It is understood that it may not be possible to place all receiving units 14 within the near-field of the transmitting unit 12. As illustrated in FIG. 1B, in order to deliver energy to receiving units 14 outside of the near-field (e.g., receiving unit $14_e$) one or more repeaters 18 may be used. The one or more repeaters 18 may contain an antenna 20 which is tuned to $\omega_s$. Each repeater may be a high quality antenna with a Q factor greater than 100. The repeater 18 may draw energy from the transmitting unit 12 via the antenna 20 in the form of an induced current. The one or more repeaters 18 may use the induced current to produce a second energy field using the antenna 20. Alternatively, the second energy field may be produced using a second antenna (not shown). The second energy field may be used to induce an alternating current in the receiving unit $14_e$. The receiving unit $14_e$ may include a transducer which may use the induced alternating current to store energy in a power storage device, such as battery or capacitor. Alternatively, the transducer may use induced alternating current to power electronic components within the receiving unit $14_e$. It is understood that the antenna 20 or second antenna (not shown) may produce a near-field in all directions (omni-directional) or may produce a near-field targeted towards a specific direction (directional).

The network 10 may also be designed to provide periodic data transfer. In a system designed for periodic data transfer, signals transmitted by each of the devices 11 may be modulated time-varying signals which carry data. One example of a data network layout includes one or more receiving units 14 placed within the near-field of a transmitting unit 12. Each of the receiving units 14 may be capable of communicating to the transmitting unit 12 and/or the other receiving units 14. It is understood that receiving units which may be out of near-field of the transmitting unit 14 may be reached using one or more repeaters 18 in the manner described above. In another example, a receiving unit 14 may be placed far-field of the transmitting unit 14 and utilize the radiative field of the transmitting unit 14 for communication. Such far-field communication is achieved in a manner similar to far-field communication techniques known to those of ordinary skill in the art.

Each receiving unit 14 may have an electronic identification (ID) that is unique to that receiving unit 14 on the network 10. The ID acts as an identifier for a particular receiving unit 14 on the network and allows a receiving unit 14 on the network to identify other receiving units 14 on the network 10 for communication. To initiate a data-transfer session, a transmitting device would identify a receiving device with its ID and begin communications using an initiation instruction. The data transfer would occur using, a specified modulation scheme. Security protocols may be used to ensure that the data transferred by and stored in the devices are secure and not accessible to unauthorized devices which are not present in the designed network 10.

Periodic data communication may occur between a transmitting unit 12 and one or more receiving units 14 or between a receiving unit 14 and one or more other receiving units 14. In transmitting unit-receiving unit communications, a transmitting unit 12 may identify a particular receiving unit 14 based on its ID and initiate a communication session. Alternative, a receiving unit 14 may identify a transmitting unit 12 based on its ID and initiate a communication session. The communication session may be terminated by either the transmitting unit 12 or the receiving unit 14.

In receiving unit-receiving unit communications, two receiving units 14 may connect directly with each other in direct communication. Alternatively, two receiving units 14 may connect with each others using the transmitting unit 12 as an intermediary. In such cases, each receiving unit 14 may connect to the transmitting unit 12 and the transmitting unit 12 would receive information from one receiving unit 14 and transmit it to the other receiving unit 14. In another alternative, two receiving units 14 may communicate using one or more repeaters 18 where the one or more repeaters 18 may receive a signal from a receiving unit 14 and transmit it to another receiving unit 14. The one or more repeaters 18 may be one or more stand-alone resonant antennae and may be independent of any circuitry.

The system and method illustrated in FIG. 1A and FIG. 1B to efficiently transfer energy between two or more devices may be used in a variety of applications in order to operate household appliances such as vacuums, irons, televisions, computer peripheral devices; mobile devices; military applications such as surveillance equipment, night vision devices, sensor nodes and devices; transportation applications such as sensors designed to monitor automobile or train performance and safety; aerospace applications, such as control of flaps, rudders, or landing gear; space technology; naval applications such as applications to power unmanned watercraft; traffic control applications such as road imbedded sensors; industrial applications; robotic networks; and medical devices.

The system and method described to efficiently transfer energy between two or more devices may also be applied to a system and method for the artificial internal stimulation of human tissue. As will be described more fully herein, such a system generally comprises a first implantable device, a second implantable device, and one or more external devices which interact to provide stimulation to human tissue. The second implantable device stimulates human tissue with one or more multiple leads and receives power and communication wirelessly from the first implantable device. The first implantable device stores power, performs computations, and receives power and communications from the external device. The one or more external devices are external to the body and may be used to transmit power, data and/or perform computations. The first implantable device, the second implantable device, and one or more external device may include one or more antennas that enable wireless transmission and reception of power and communications using high-Q resonant inductive coupling.

The system and method described herein may be used to provide electrical stimulation for the treatment and management of chronic intractable pain, heart arrhythmia and other medical conditions in which stimulation may be beneficial. For example, the system and method may be used as a neural stimulator, such as a spinal cord stimulator to provide stimulation to the spinal cord of a patient for the treatment of certain medical afflictions, including failed back surgery syndrome, complex regional pain syndrome and refractory pain due to ischemia. In addition, the system and method may be used as a deep brain stimulator to provide therapeutic benefits in the treatment of chronic pain, affective disorders, and neurological disorders, including depression, Parkinson's disease, essential tremor, Alzheimer's disease, obesity, and dystonia. The system and method may also be used as a peripheral nerve stimulator to provide pain relief or muscle control. In addition, the system and method may be used as a vagus nerve stimulator to control incontinence. The system and method may also be used as a cardiac stimulator to treat patients with irregular heart rhythms by controlling the pulse at which the heart beats. Such systems include pacemakers, implanted cardiac defibrillators, or a combination of such devices. It is also contemplated that the system and method may be used for the stimulation of other organs, muscles, or nerves, such as for example, as bowel stimulators and muscle stimulators.

FIG. 2A illustrates a high-level block diagram of a system 100 for stimulating human tissue. The system may include an external controller 102, an internal controller 104, and an internal stimulator 106. The external controller 102 transmits power and control information to the internal controller 104 and/or internal stimulator 106. In one example, based on the received information, the internal controller 104 may transmit power and control information to the internal stimulator 106. Based on the power and control information received from the internal controller 104, the internal stimulator 106 may directly or indirectly stimulate human tissue. Alternatively, the external controller 102 may transmit power and control information directly to the internal stimulator 106.

Preferably, the electronic components of the external controller 102, internal controller 104, and internal stimulator 106 each will be encased in a polymer or non-magnetic metal housing, such as for example, titanium or niobium. The resonating structures of the external controller 102, internal controller 104, and internal stimulator 106 may be encased in a bio-compatible polymer housing, such as for example silicone or PDMS. The housing for the electronic components and the housing of the resonating structures may directly or indirectly attached to one another. The external controller(s) 102 may be any of a variety of configurations, such as a portable unit that is suitable to be placed in a bag, pocket, or other user-wearable configuration such as a belt or bracelet. It is understood that the external controller(s) 102 does not have to interact with the internal controller 104 at all times.

As shown in FIG. 2B, the system 100 may also include one or more repeaters 108 to relay power and control information between the internal controller 104 and the internal stimulator 106. The one or more repeaters 108 may be used to increase the spatial range of the system 100 thereby allowing a greater distance between the internal controller 104 and the internal stimulator 106. Each repeater 108 may be an antenna with a Q factor greater than 100.

Figure 3A:
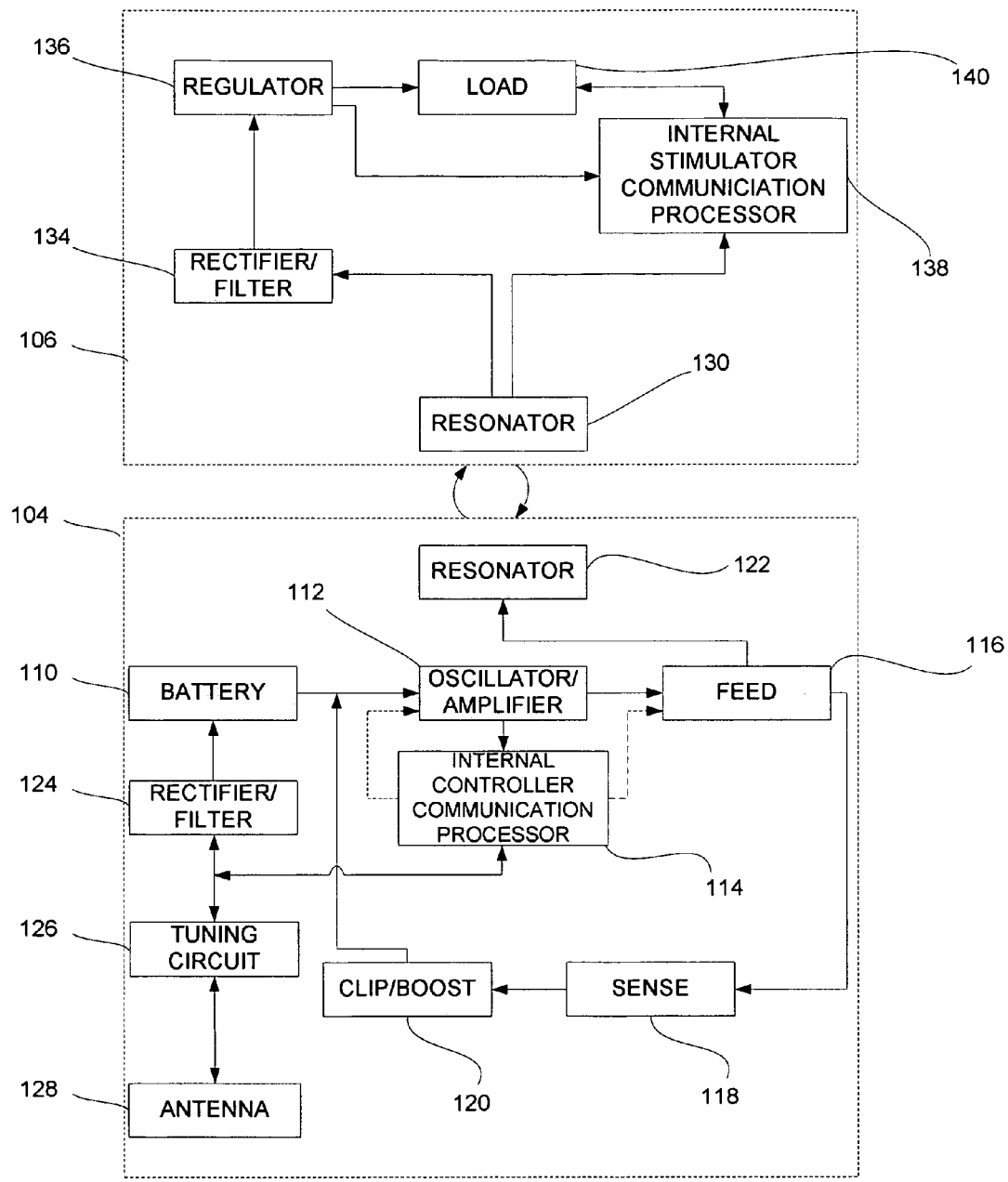
FIG. 3A illustrates an example of a block diagram for internal stimulator and an internal controller.

FIG. 3A illustrates a detailed block diagram of an exemplary internal stimulator 106 and internal controller 104. The internal stimulator 106 and internal controller 104 may be implanted in the human body to provide medical treatment to human tissue. Power and control information may be transferred between the internal controller 104 and internal stimulator 106.

The internal controller 104 may include a battery 110, an oscillator and amplifier component 112, an internal controller communications processor 114, a feed component 116, a current sense component 118, a clip-boost component 120, a resonator component 122, a rectifier and filter component 124, a tuning circuit 126, and an antenna 128 for bi-directional telemetry with an external controller 102.

The antenna 128 in the internal controller 104 may be used for bi-directional communication with the external controller 102. Power and control information may be transmitted between the internal controller 104 and the external controller 102 through the antenna 128. The internal controller 104 may also include a tuning circuit 126. The tuning circuit may include capacitive and inductive elements to tune the antenna 128 to a desired operating frequency to provide efficient communication with the external controller 102.

The battery component 110 may include a rechargeable battery and battery control circuit. The battery component 110 stores energy received from a primary power source. The primary source may be part of or separate from the external controller 102 and provides energy to the battery component 110. The primary power source may be a battery located in the external controller or other sources of energy. The battery control circuit may be used to provide energy to the other components in the internal controller 104 via the connection to the oscillator/amplifier component 112. The battery control circuit may also be used to charge the battery as described below. It is understood that the other components in the internal controller 104 may be directly or indirectly connected to the battery for energy transfer.

The battery component 110 may include a non-rechargeable or a rechargeable battery. In systems using a rechargeable battery, energy in the rechargeable battery may be replenished when the stored energy is below a certain desired capacity. The rechargeable battery may be charged using indirect recharging methods, such as inductive coupling between the external controller 102 and the internal controller 104. For example, the antenna 128 may receive energy from the external controller 102. The energy may be rectified to single polarity and filtered to a direct current signal using the rectifier and filter component 124. The direct current signal may be used by the recharging circuitry in the battery component 110 to charge the rechargeable battery. It is understood that systems utilizing a non-rechargeable battery will not require the battery to be charged.

It is also contemplated the other methods of recharging the battery may be used, such as an optical link, laser, or highly directive radio-frequency beam. It is also contemplated that alternative sources of energy may be used to recharging the battery, such as the conversion of kinetic energy into electrical energy. This may be accomplished by converting movement into energy. For instance, the internal controller 104 may be attached to the body may use body movements to spin a rotor that causes a generator to produce an alternating current. The energy in the alternating current may be stored in the battery component 110. In addition, a thermoelectric generator may be used to recharge the battery by using heat energy, such as that extracted from heat gradients in the body or that dissipated by the internal controller 104. In this manner, a portion of heat energy which would have otherwise been dissipated to the surrounding tissue is recycled as electrical energy thereby improving the efficiency and safety of the system.

The oscillator/amplifier component 112 may include an oscillator, an amplifier, and connections to the battery component 110, the internal controller communications processor 114, and the feed component 116. The oscillator/amplifier 112 may be a transistor operating in Class-E mode. The oscillator in the oscillator/amplifier component 112 may be used to convert the direct current supplied from the battery component 110 into alternating current. The amplifier in the oscillator/amplifier component 112 may be used to modify the alternating current to achieve the desired current and voltage. The oscillator/amplifier component 112 outputs the alternating current to the feed component 116.

The internal controller communications processor 114 may include a modulation circuit and connections to the oscillator/amplifier component 112 and the feed component 116. The modulation circuit of the internal controller communications processor 114 may be used to modulate the carrier signal with the appropriate power and control information intended for the internal stimulator 116. The modulation may occur before the signal enters the oscillator/amplifier component 112 by varying the amplitude and/or frequency of the signal flowing into the oscillator/amplifier component 112. Alternatively, the modulation may occur after the signal flows out of the oscillator/amplifier component 112 by varying the amplitude and/or frequency of the signal flowing into the feed component 116.

In one aspect of the present example, the internal controller communications processor 114 may also be used to facilitate communication between the internal controller 104 and the external controller 102. The external controller 102 may transmit control information to the internal controller 104. One type of control information may be stimulation parameters for a one or more stimulation sets. The stimulation parameters may include the identity of a particular electrode(s) to control, the pulse amplitude to apply at the selected electrode(s), and the pulse width and frequency of the stimulation that is to be applied, and the pulse pattern to apply at the selected electrode(s). Of course, it is understood that control information may include other types of information needed to control the various components in the internal controller 104 and/or the internal stimulator 106. A user may input the control information into the external controller 102 for transmission to the internal controller 104, and ultimately, to the internal stimulator 106. Alternatively, the external controller 102 may store the control information in memory for subsequent transmission to the internal controller 104. When control information needs to be transmitted by the external controller 102, the external controller 102 may initiate a data transmission session. During the data transmission session, a modulated signal containing control information is transmitted from the external controller 102. Once the communication of data is complete, the internal controller 104 and/or external controller 102 will terminate the data transmission session.

The antenna 128 in the internal controller 104 may receive from the external controller 102 the modulated signal carrying control information. The internal controller communications processor 114 may demodulate the received signal and extract the control information from the modulated signal. The internal controller communications processor 114 may include a memory location or be coupled to a memory location to store the control information received from the external controller 102. In this manner, control information is transmitted from the external controller 102 to the internal controller 104 only on a periodic basis, such as when the control information stored in the internal controller communications processor 114 must be modified. It is understood that control information for a plurality of different stimulation sets may be stored in the memory location.

The feed component 116 may contain a feed circuit and connections to the oscillator/amplifier component 112, the sense component 118, and the resonator component 122. The feed component 116 may be wirelessly coupled to the resonator 122, such as by inductive coupling, or may be connected to the resonator component 122 with a wire. The feed component 116 receives instructions from the internal controller communications processor 114 and drives the resonator 122. Preferably, the feed circuit is tunable such that the resonator component 122 produces a conjugate and optimal match to the oscillator/amplifier component 112 in the internal stimulator 106. When the feed component 116 is wirelessly coupled to the resonator component 122, the conjugate match may also be achieved by varying the coupling coefficient between the feed component 116 and the resonator component 122. The feed circuit may be tuned using capacitive and inductive elements.

The current sense component 118 includes current sense circuitry and connections to the feed component 116 and the clip/boost component 120. The current sense circuitry senses the current flowing through the feed component 116 and determines the value of the current. The current sense circuitry conveys the determined value of the current to the clip/boost component 120.

The clip/boost component 120 includes power clipping and boosting circuitry and connections to the oscillator and amplifier component 112 and the current sense component 118. The clip/boost component 120 may be used to control the signal strength at the resonator component 122 such that it remains within a predetermined power range. Preferably, the signal strength is maintained within the predetermined power range by determining the amount of current driving the antenna and modifying the current via the connection to the oscillator and amplifier component 112. The clip/boost component 120 may reduce the signal amplitude if the amplitude is higher than the predetermined power range and may boost the signal amplitude if the amplitude is lower than the predetermined power range.

The resonator component 122 includes a resonant structure, such as an antenna, and a tuning circuit. The resonant structure produces electromagnetic fields that may be used to wirelessly transfer power and/or control information from the internal controller 104 to the internal stimulator 106. The resonant structure may be used to convert the current received from the feed component 116 into electromagnetic fields to convey power and control information to the internal stimulator 106. As will be described herein, the resonant component 122 is preferably designed with a high quality factor and tuned to the same resonant frequency as the resonant component 130 to achieve efficient transfer of power. The resonator component 122 may include tuning circuitry to tune the resonator component 122 to the operating frequency. The tuning circuit may include capacitive and inductive elements.

In one aspect of the present example, control information may be periodically transmitted from the internal controller 104 to the internal stimulator 106 and stored in memory at the internal stimulator 106. When control information needs to be transmitted from the internal controller 104 to the internal stimulator 106, either the internal controller 104 or internal stimulator 106 may initiate a data transmission session. The control information may be the control information received from the external controller 102 and stored in memory or may be control information previously stored in memory, in a manner known to those of ordinary skill in the art. During the data transmission session, a modulated signal containing the control information is generated by the internal controller 104, and preferably by the internal controller communications processor 114. The generated signal containing the control information is transmitted by the resonator 122. Once the communication of data is complete, the internal controller 104 and/or internal stimulator may terminate the data transmission session.

The internal stimulator 106 may include a resonator component 130, a rectifier and filter component 134, a voltage regulator 136, an internal stimulator communications processor 138 and a load component 140, as illustrated in FIG. 3A. The internal stimulator 106 may also include a pickup component 132, as illustrated in FIG. 3B.

The resonator component 130 may include a resonant structure, such as an antenna and a tuning circuit. The resonant structure receives an electromagnetic signal from the resonant structure in the internal controller 104 and converts the electromagnetic signal into electric currents. The current may be used to provide power to the internal stimulator 104. In this manner, power is transferred from the internal controller 104 to the internal stimulator 106 and the resulting current is supplied to the other components in the internal stimulator 106. As will be described herein, the resonant component 130 is preferably designed with a high quality factor and tuned to the same resonant frequency as the resonant component 122 to achieve efficient transfer of power from the internal controller 104 to the internal stimulator 106. The resonator component 130 may include tuning circuitry to tune the resonator component 130 to the operating frequency. The tuning circuit may include capacitive and inductive elements.

The wireless power transfer between the internal controller 104 and the internal stimulator 106 is achieved using a high-Q resonant inductive coupling scheme. The high-Q inductive coupling scheme is accomplished using electromagnetic coupling of two or more resonant components 122, 130 tuned to the same resonant frequency. The resonance may be achieved either via self-resonance of the antenna element or via discrete inductive and capacitive elements. The resonant components 122, 130 are tuned to resonate with each other. The high-Q resonant inductive coupling scheme permits relatively close to mid-distant placement of the resonant components 122, 130 such that their electromagnetic fields couple. The high-Q resonant coupling of the electromagnetic fields permits efficient energy transfer between the two resonant components.

Figure 3B:
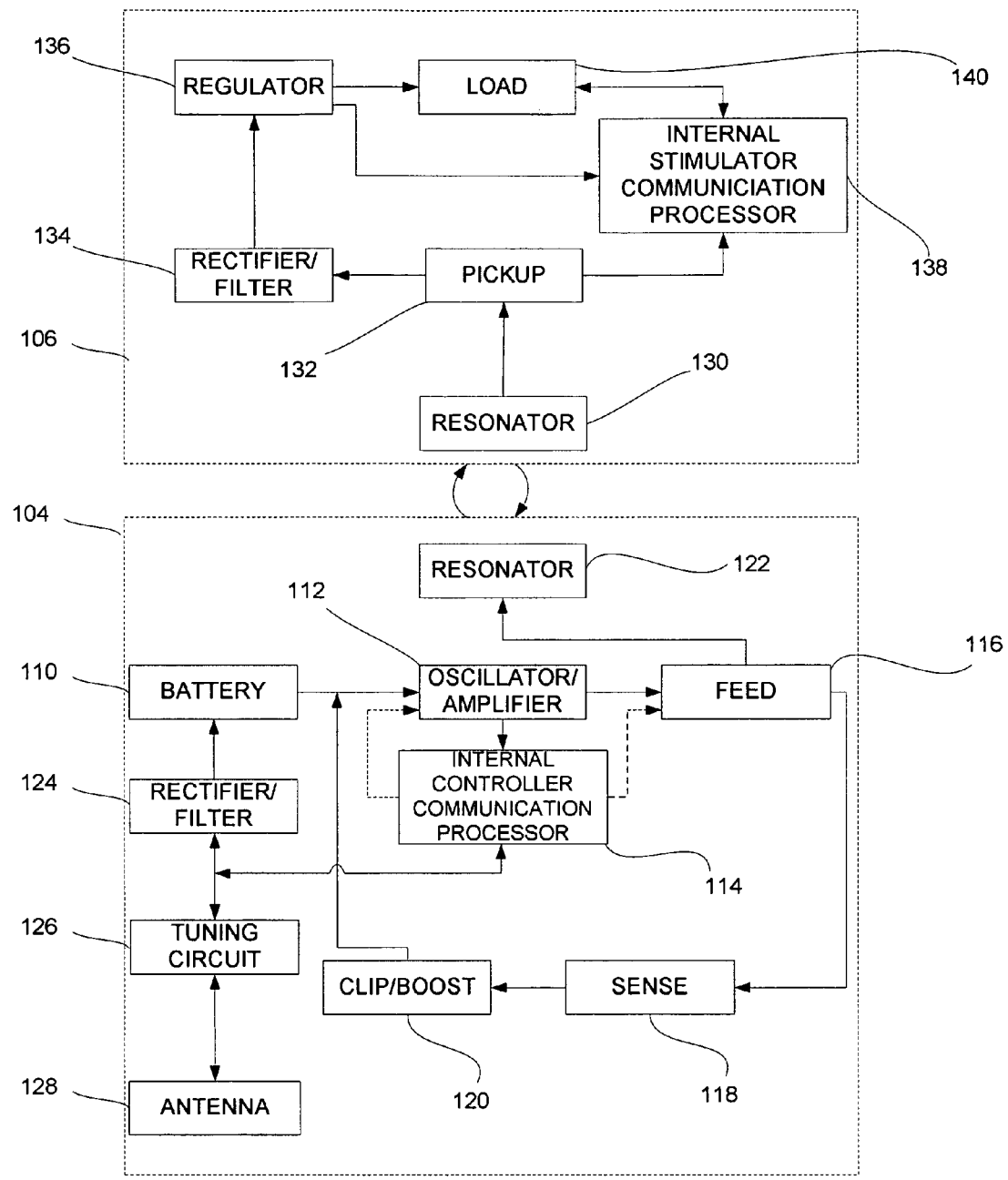
FIG. 3B illustrates an example of a block diagram for internal stimulator and an internal controller.

As illustrated in FIG. 3B, the resonator component 130 may be coupled to a pickup component 132. The pickup component 132 may be wirelessly coupled to the resonator 130, such as by inductive coupling, or may be connected to the resonator component 130 with a wire. The pickup component 132 may include receiving circuitry and connections to the resonant component 130, the rectifier and filter component 134, and the internal stimulator communications processor 138. The pickup component 132 may be used to receive current from the resonant component 130 and transfer the current to the other components in the internal stimulator 106. The pickup component 132 may be tunable so that the resonator component 122 in the internal controller 104 produces a conjugate and optimal match to the pickup component 132. In this manner, power transfer between the internal controller 104 and the internal stimulator 106 is maximized. Alternatively, the resonator component 130 may be directly connected to the internal stimulator communications processor 138 and the rectifier and filter component 134.

The rectifier and filter component 134 may include a rectifier circuit and filter circuitry and connections to the pickup component 132 and the voltage regulator 136. In systems that do not include the pickup component 132, the rectifier and filter component 134 may be connected directly to the resonator component 130, as illustrated in FIG. 3A. The rectifier circuit receives alternating current from the resonator component 130 via the pickup component 132 and converts the received alternating current into a direct current. The filter circuitry may include a low-pass filter to smooth the current. The resulting direct current may be supplied to other components in the internal stimulator 104, such as the load component 140.

Figure 4A:
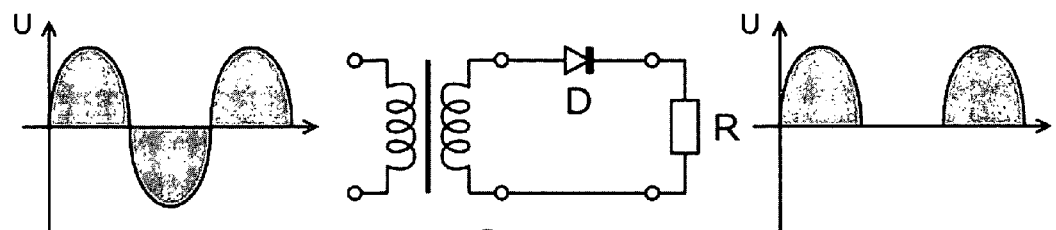
FIG. 4A illustrates an example of a circuit schematic for one a half-wave rectifier.
Figure 4B:
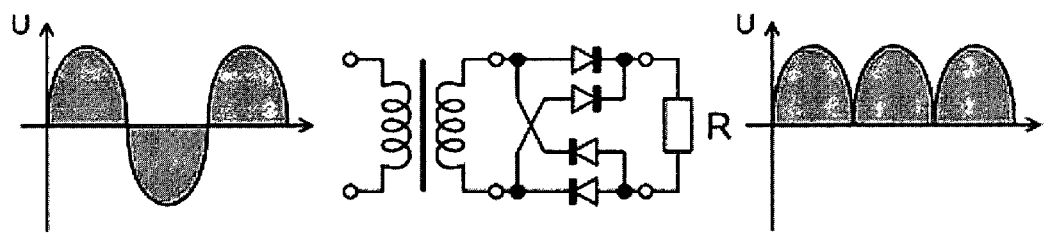
FIG. 4B illustrates an example of a circuit schematic for a non-center tapped full-wave rectifier.
Figure 4C:
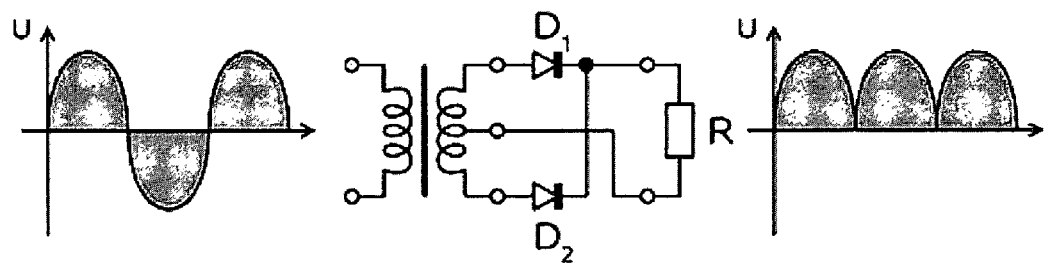
FIG. 4C illustrates an example of a circuit schematic for a center tapped full-wave rectifier.

The rectifier circuit may be a half-wave rectifier or a full-wave rectifier. FIG. 4A illustrates a circuit schematic for one type of half-wave rectifier 142 that may be used. The half-wave rectifier 142 includes a single diode 144 connected in series with a coil 146. FIG. 4B illustrates a circuit schematic for a non-center tapped full-wave rectifier 148 that may be used in the present system 100. The non-center tapped full-wave rectifier 148 includes four diodes 150 arranged in a bridge-rectifier configuration. FIG. 4C illustrates a circuit schematic for a center tapped full-wave rectifier 152 that may be used in the system 100. The center tapped full-wave rectifier 152 includes two diodes 150 with a center-tapped coil 154. A half-wave rectifier may be used for systems with a low voltage requirement and low coupling coefficients. Systems that require high voltage may use a full-wave rectifier or a voltage multiplier. In systems operating at higher frequencies, such as 2 MHz or greater, the diodes illustrated in FIGS. 4A-4C may be replaced with Schottky rectifiers.

The voltage regulator component 136 may include a voltage regulator and connections to the rectifier and filter component 134 and the load component 140. The voltage regulator receives the direct current from the rectifier and filter component 134 and uses the received current to generate one or more constant voltages. For example, one constant voltage may be supplied to the load component 140 and one constant voltage may be supplied to the internal stimulator communication processor 138. The value of the constant voltage(s) supplied to the load component 140 and the internal stimulator communications processor 138 depend on the requirements of each of those components. The voltage regulator prevents the load component 140 and internal stimulator communications processor 138 from being damaged due to any fluctuations in the rectified voltage outputted by the rectifier and filter component 134.

The internal stimulator 106 may also include a thermoelectric generator (not shown) used to capture heat energy, such as that extracted from heat gradients in the body. The thermoelectric generator uses the captured heat to generate a voltage which may be used to supplement power received from the internal controller 104. In this manner, a lesser amount of power may be transferred from the internal controller 104 to the internal stimulator 106, while still providing the necessary power to the load 140.

The internal stimulator communications processor 138 may contain signal modulation and demodulation circuitry and connections to the load component 140 and the pickup component 132. The internal stimulator communications processor 138 may be used to recover any control information received by the resonator component 130 during a data transmission session. The recovered control information may be stored in memory within the internal stimulator communications processor 138 or in memory coupled to the internal stimulator communications processor 138. The control information may include stimulation parameters for a one or more stimulation sets that are applied by the stimulation electrodes 158. The stimulation parameters may include the identity of a particular electrode(s) to control, the pulse amplitude to apply at the selected electrode(s), and the pulse width and frequency of the stimulation that is to be applied, and the pulse pattern to apply at the selected electrode(s).

Figure 5:
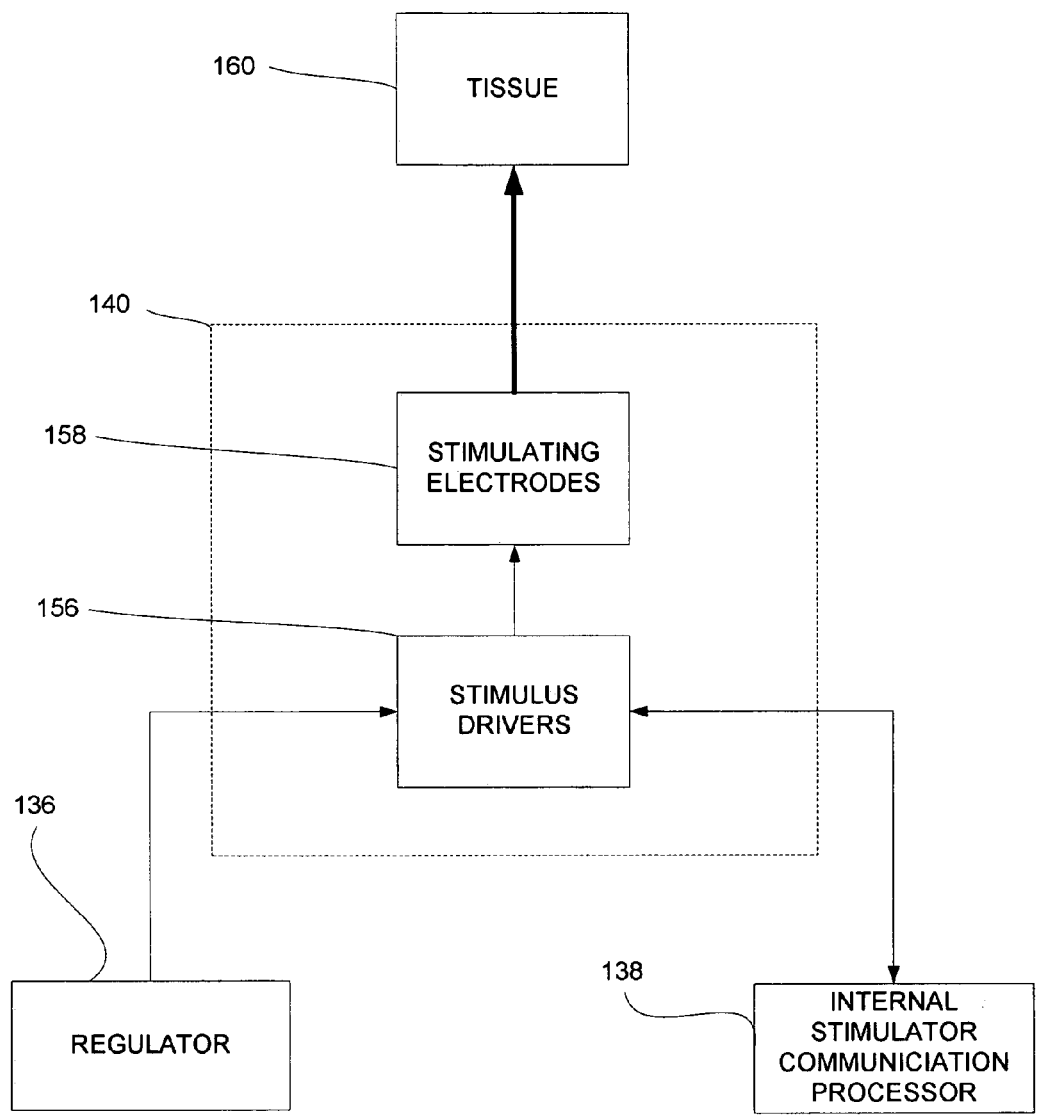
FIG. 5 illustrates an example of a block diagram for a portion of the internal stimulator.

The load component 140 is connected to the voltage regulator component 136 and the internal stimulator communications processor 138 to perform a specific task, such as providing stimulation to tissue. As shown in FIG. 5, the load component 140 may include a stimulus driver 156 coupled to stimulating electrodes 158 to provide stimulation to tissue 160. The load component 140 may also include a feedback circuit for detecting sensory information. The sensory information may include, for example, diagnostic information such as tissue resistance, electro-physiological actions such as neural and myocardial action potentials, and other electrical and non-electrical characteristics. The feedback circuit may detect the sensory information and transmit the sensory information to the internal stimulator communications processor 138. The internal stimulator communications processor 138 may store the sensory information in a memory location. The memory location may be in the internal stimulator communications processor 138 or a memory location coupled to the internal stimulator communications processor 138.

In one aspect of the present example, the sensory information may be periodically transmitted from the internal stimulator 106 to the internal controller 104 stored in a memory location at the internal controller 104. When sensory information needs to be transmitted from the internal stimulator 106 to the internal controller 104, either the internal stimulator 106 or internal controller 104 may initiate a data transmission session. During the data transmission session, a modulated signal containing the control information is generated by the internal stimulator 106, and preferably by the internal stimulator communications processor 138. The generated signal containing the sensory information is transmitted by the resonator component 130. The internal controller 104 may receive the signal via the resonator component 122 and demodulate the signal to recover any sensory information received during the data transmission session. The recovered control information may be stored in memory within the internal controller communications processor 114 or in memory coupled to the internal controller communications processor 114. Once the communication of the sensory information is complete, the internal controller 104 and/or internal stimulator may terminate the data transmission session.

The internal controller 104 may transmit data, such as sensory information received from the internal stimulator 106, to the external controller 102. When sensory information needs to be transmitted to the external controller 102, either the internal controller 104 or external controller 102 may initiate a data transmission session. During the data transmission session, a modulated signal containing the sensory information is generated by the internal controller 104, and preferably by the internal controller communications processor 114. The generated signal containing the sensory information is transmitted by the antenna 128. The external controller 102 detects the signal transmitted from the antenna 128 and demodulates the signal to extract the sensory information. Once the communication of sensory information is complete, the internal controller 104 and/or external controller 102 may terminate the data transmission session.

It is contemplated that one of several types of modulation schemes may be implemented to facilitate wireless communication of data, including control information and sensory information, between the internal controller 104 and the external controller 102 and also between internal controller 104 and the internal stimulator 102. For example, frequency-shift keying/frequency modulation (FSK/FM), pulse width modulation (PWM), amplitude modulation (AM) or On Off Keying (OOK) may be utilized.

In one example, an OOK modulation scheme is used to facilitate communication of control information between the internal controller 104 and the internal stimulator 106. When the OOK modulation scheme, a fixed number of cycles at the operating frequency $\omega$ will denote a "1" or a "0" when the signal is ON or OFF, respectively. The basic operation of the OOK modulation scheme will now be described below. Under normal operating conditions, a continuous signal at $\omega$ is generated by the internal controller 104 which magnetically couples to the resonator component 130 in the internal stimulator 106 and subsequently the load component 140 for operation of the internal stimulator 106. At a predetermined time, a pre-set word pattern is generated to indicate the beginning of communication of control information. A bit sequence is generated at the internal controller 104. The bit sequence identifies a particular electrode to control, the pulse amplitude to apply at the selected electrode, and the pulse width and frequency of the stimulation that is to be applied. The bit sequence is subsequently transmitted from the internal stimulator 104 to the internal stimulator 106 and decoded by an internal stimulator communications processor 138. Once the communication of control information is complete, the internal controller 104 will generate a signal at frequency $\omega$ until further communication is required.

Figure 6:
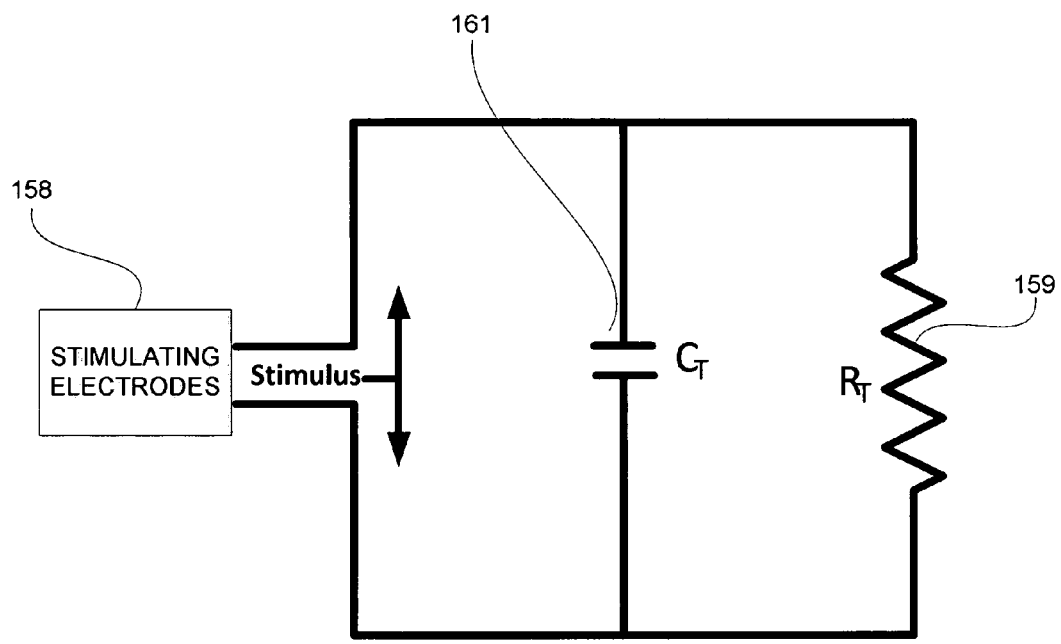
FIG. 6 illustrates an example of a schematic of the tissue that may be stimulated using the stimulating electrodes.

FIG. 6 illustrates a schematic of the tissue 160 that may be stimulated using the stimulating electrodes 158. The tissue 160 may be any type of human tissue, such as, for example, connective tissue, dural tissue, visceral muscle tissue, skeletal muscle tissue, cardiac muscle tissue, neural tissue, epithelial tissue, bone tissue, cerebrospinal fluid, or any other type of human tissue known to those of ordinary skill in the art. Additionally, although the example provided herein discuss human tissue, the present system and method may also be used with other animal tissue known to those of ordinary skill in the art. The stimulated tissue 100 inherently includes a resistance 159 and capacitance 161. The values of the resistance 162 and capacitance 164 may be determined based on the appropriate power and stimulation necessary to provide the appropriate medical treatment. The stimulating electrodes 158 provide a stimulus to the stimulated tissue 160.

In one example, the tissue 160 that is stimulated may be A-Beta neural fibers, which are responsible for gross touch, vibration, and proprioception functions. The maximum diameter of such fibers is generally 15 μm. It is preferable that the tissue fibers which are to be stimulated have a diameter of at least 10.7 μm, however, it is contemplated that any fibers having a diameter of less than 10.7 μm can be stimulated. The A-Beta neural fibers are located in the dorsal column in the spinal cord, approximately 0.20-0.25 mm below the pia mater. Preferably, the tissue 110 that is to be stimulated includes up to approximately 65 fibers in the dorsal column, which innervates up to approximately 12 dermatomes. It is preferred that 4 to 5 fibers are specific to a targeted dermatome. It is also contemplated that the stimulation of only 1 fiber may achieve paresthesia.

Figure 7A:
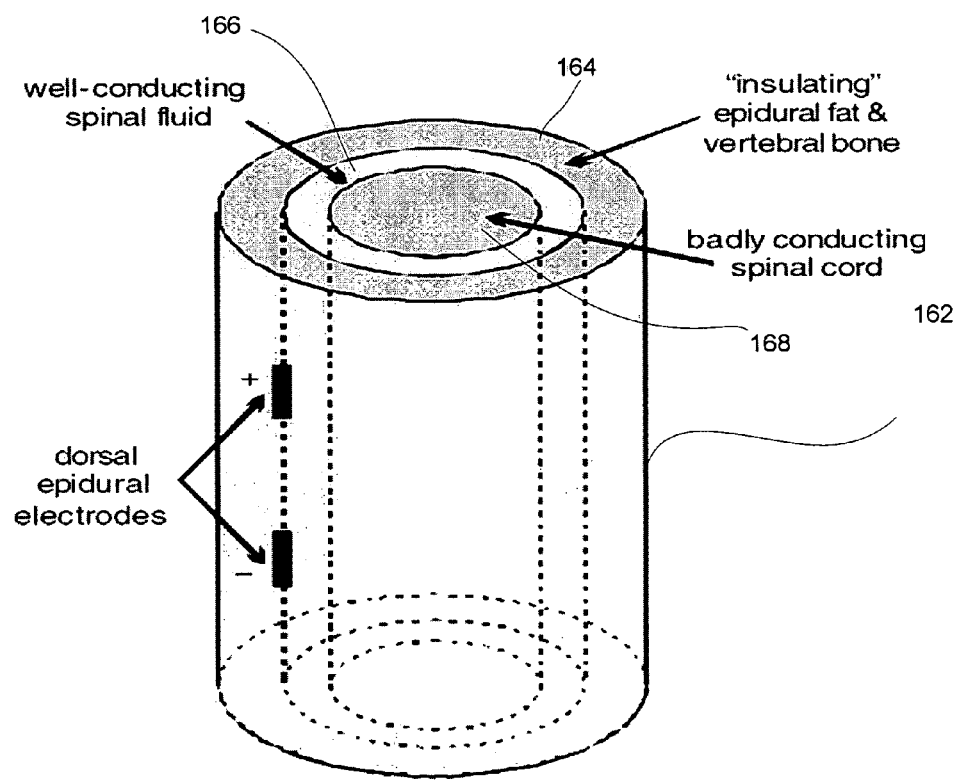
FIG. 7A illustrates an example of an anatomical model of the tissue that may be stimulated using the stimulating electrodes.

FIG. 7A illustrates an anatomical model of tissue 160 that may be stimulated by the stimulating electrodes 158. For the purposes of illustration, the stimulated tissue 160 is neural and surrounding tissue of the spinal column 162 and is modeled as 3 concentric cylinders 164, 166, 168. The spinal column 162 includes an outer insulating vertebral bone and epidural fat 164, a middle conductive cerebrospinal fluid 166, and a spinal cord 168. The transverse resistance of the outer insulating vertebral bone and epidural fat 164 and spinal cord 168 of the spinal column 162 is greater than the longitudinal resistance of the outer insulating vertebral bone and epidural fat 164 and spinal cord 168 of the spinal column 162. The transverse resistance and the longitudinal resistance are substantially greater than the resistance provided by the cerebrospinal fluid 166. One approximation of tissue resistivity and normalized values are provided in the Table 1:

TABLE 1

Approximate Tissue Resistivity (R) and Normalized Values ($R_{norm}$)

| Structure | | R(Ω · cm) | $R_{norm}$ |
|---|---|---|---|
| Spinal gray matter | | 435 | 7.4 |
| Spinal white matter | Transverse | 1205 | 20.4 |
| | Longitudinal | 167 | 2.8 |
| Cerebrospinal fluid | | 59 | 1.0 |
| Epidural fat | | 2500 | 42.4 |
| Vertebral bone | | 2500 | 42.4 |

Figure 7B:
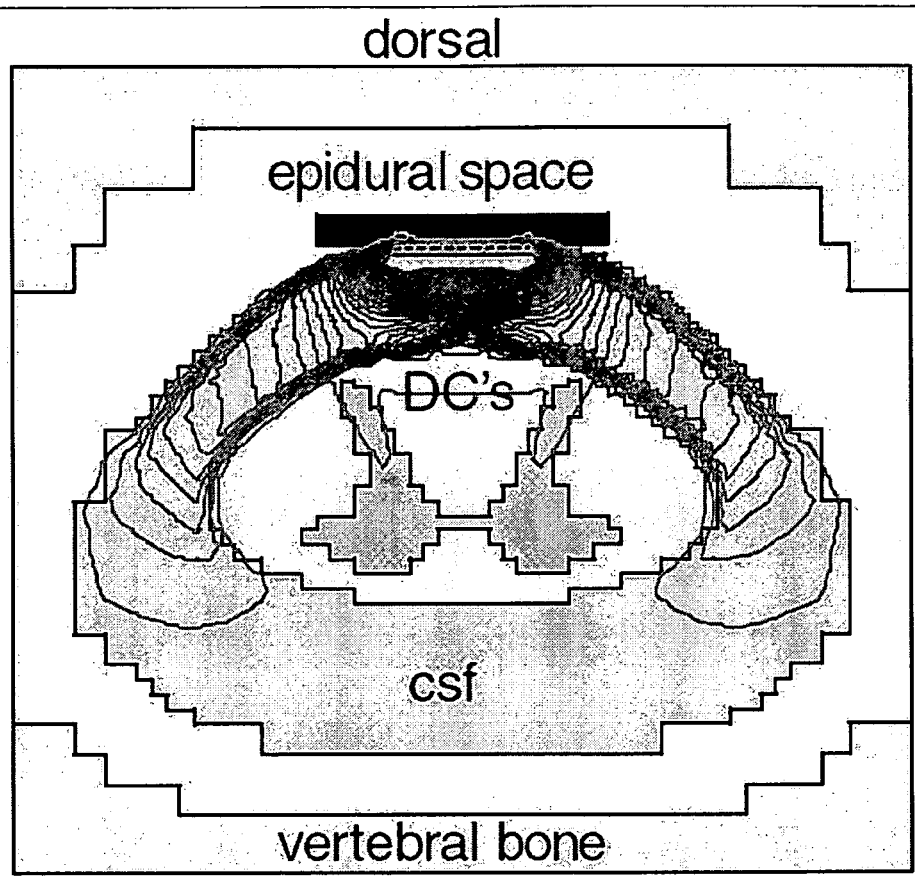
FIG. 7B illustrates a current density mode numerical model.

Due to the nature of the resistances, it is preferred that the stimulating electrodes 158 are positioned to electrically contact the middle conductive cerebrospinal fluid 166. The relatively low resistance of the cerebrospinal fluid 166 as compared to the transverse and longitudinal resistance allows a greater percentage of current to flow through the cerebrospinal fluid 166 as compared to the other portions of the spinal cord. It is preferable that approximately 90% of the current discharged from the stimulating electrodes 158 flow through the cerebrospinal fluid 166 and 10% of the current flow through the outer insulating vertebral bone and epidural fat 164 and spinal cord 168 of the spinal column 162. The current discharged from the stimulating electrodes 158 preferably stimulates five to six DC neurons, however it is understood that typically, only one of the neurons innervates the dermatome of interest. A current density mode numerical model is illustrated in FIG. 7B. Based on the numerical model, it is understood that the current is substantially within the cerebrospinal fluid 134.

As discussed above, the stimulating electrodes 158 provide electrical stimulation to the tissue 160. To provide electrical stimulation to the tissue, the stimulus drivers 156, regulator component 136 and internal stimulator communications processor 138 operate to provide a pulsed current to the stimulating electrodes 158. In one aspect of the present example, one objective of the electrical stimulation provided to the tissue 160 is to relieve pain for the entire area in which a patient is experiencing pain. Another objective is to focus the electrical field created by the stimulation on the appropriate section of the dorsal column. Typically, for bilateral pain, the electric field is focused on the spinal cord midline; for unilateral pain the electric field is focused up to 1 mm lateral to the midline, and for segmental pain, the electric field is focused further than 1 mm lateral to midline so as to stimulate a specific dorsal root. It is also contemplated that other distances lateral to the midline may used to provide stimulation for unilateral or segmental pain. Another objective of the stimulation may be to stimulate the A-beta fibers specific to the dermatome where the patient is experiencing pain and to also overcome the paresthesia threshold but not the discomfort threshold.

Preferably the stimulus parameters include at least a therapeutic range and pulse parameters. The therapeutic range may be calculated according to the following equation:

$$\text{Therapeutic Range} = \frac{\text{Discomfort Threshold}}{\text{Paresthesia Threshold}} - 1$$

where Discomfort Threshold and Paresthesia Threshold are expressed in Volts.

In one embodiment, the pulse parameters may include a current pulse width of 30-500 μs, a pulse frequency of 10-1200 Hz, a pulse current of 0.1-25 mA, and a tissue impedance of 1 kΩ. Other values for the pulse width, pulse frequency, current pulse width, and tissue impedance may be utilized without departing from the scope of the present teachings. In addition, other pulse parameters, such as polarity (i.e., monophasic or biphasic), may be provided. In one example, the maximum level of power applied to a stimulation site having a tissue impedance equal to 1 kΩ is 0.39 Watts. The power (P) applied to the stimulation may be determined based on the current amplitude (A), tissue impedance (R) current pulse width (PW), pulse frequency (f), and number of stimulation sets (S) according to the following equation:

$$P = i^2 R \cdot PW \cdot f \cdot S$$

In one example of the present embodiment, a single stimulation set may be used to provide 0.39 Watts to the tissue. In order to provide 0.39 Watts using a single stimulation set, the following parameters may be utilized:

| Parameter | Stimulation Set (S) = 1 |
|---|---|
| Amplitude (A) | 25.5 Ma |
| Current Pulse Width (PW) | 500 μs |
| Frequency (f) | 1200 Hz |
| Tissue Impedance (R) | 1000 Ω |

In another example according to this embodiment, a stimulation set of eight may be used to provide 0.39 Watts to the tissue. In order to provide 0.39 Watts using a stimulation set of eight, the following parameters may be utilized:

| Parameter | Stimulation Set (S) = 8 |
|---|---|
| Amplitude (A) | 25.5 mA |
| Current Pulse Width (PW) | 500 μs |
| Frequency (f) | 150 Hz |
| Tissue Impedance (R) | 1000 Ω |

It is contemplated that other values for the amplitude, current pulse width, frequency may be utilized without departing from the scope of the present teachings. It is also understood that the tissue impedance may be different and may affect the values of the amplitude, current pulse width, frequency. It is also understood that the number of stimulation sets and the desired power level applied to the tissue may be varied. These variations may also affect the values used for the amplitude, current pulse width, frequency. For example, in one embodiment, the tissue impedance may be 524Ω. If the same values are used for the amplitude, current pulse width, frequency, and stimulation sets provided in tables 2 and 3, the power is reduced to 0.21 Watts.

As previously described, the stimulating electrodes 158 apply stimulation to the tissue 160 according to the stimulus parameters. The stimulating electrodes 106 may be percutaneous electrodes, paddle electrodes, or any other electrodes that may be used to provide stimulation to tissue 160. The stimulating electrodes 106 may also be electrodes that provide stimulation using magnetically induced currents. It is understood that other types of electrodes known to those having ordinary skill in the art may also be used. For percutaneous electrodes, two to eight electrodes arranged in series may be used. It is also contemplated that more than eight electrodes may be used. The percutaneous electrodes may also be placed adjacent to one another for parallel stimulation. The percutaneous electrodes may be implanted using a needle or any other methods known in the art. When paddle electrodes are used, it is preferred to use between two and sixteen electrodes arranged in series or parallel. It is understood that more than sixteen electrodes may be used. The paddle electrodes may be implanted via laminectomy, using a needle, or any other methods known to those of ordinary skill in the art.

Figure 8A:
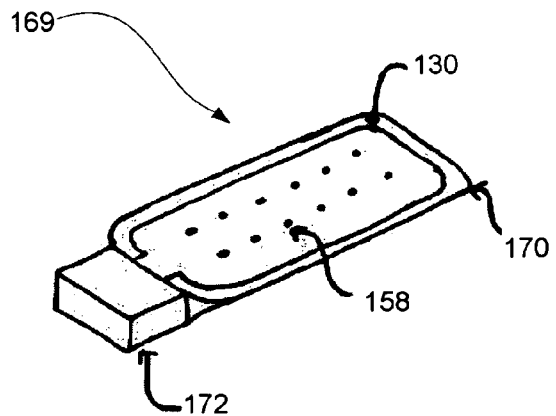
FIGS. 8A-8D illustrate examples of various internal stimulators.

FIG. 8A illustrates one example of an internal stimulator 106 in the form of a paddle-type lead 169. The paddle-type lead 169 may include an array of stimulus electrodes 158 encased in an electrode casing 170. The electrode casing 170 may be formed of highly durable bio-compatible materials, such as silicone or PDMS. The paddle-type lead 169 may also include a resonator component 130 that is integrated into the paddle-type lead 169. In addition, the pickup component 132 may also be integrated in the paddle-type lead 169. Additional circuitry, such as the rectifier and filter component 134, the voltage regulator component 136, and the internal stimulator communications processor 138 may be contained in a housing 172.

Figure 8B:
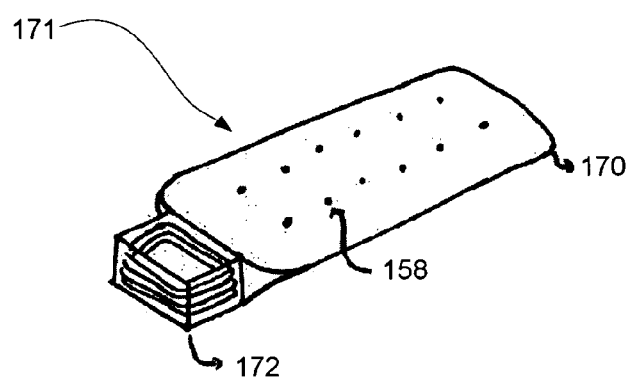

FIG. 8B illustrates another example of an internal stimulator 106 in the form of a paddle-type lead 171. The paddle-type lead 171 illustrated in FIG. 8B is similar to the paddle-type lead 169 illustrated in FIG. 8A. The paddle-type lead 171 illustrated in FIG. 8B lead may include an array of stimulus electrodes 158 that encased in an electrode casing 170. The electrode casing 170 may be formed of highly durable biocompatible materials, such as silicone or PDMS. In the paddle-type lead 171 illustrated in FIG. 8B, the resonator component 130, the pickup component 132, the rectifier and filter component 134, the voltage regulator component 136, and the internal stimulator communications processor 138 may be contained in a housing 172.

Figure 8C:
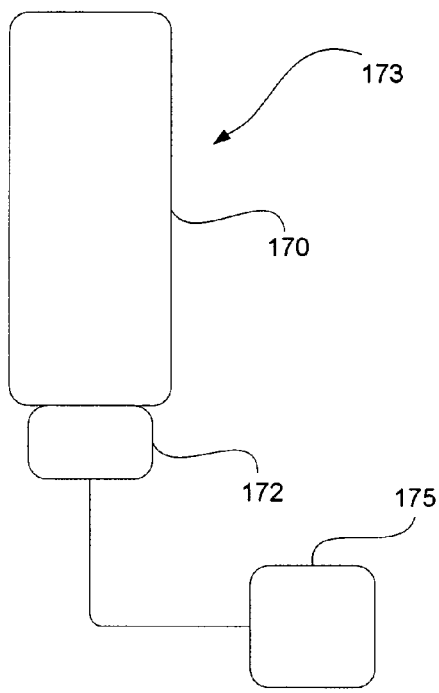

FIG. 8C illustrates an example of an internal stimulator 106 in which the paddle-type lead 173 is displaced a short distance from a housing 175 that contains the resonant component 130 and/or the pickup component 132. The paddle-type lead illustrated in FIG. 8C lead may include an array of stimulus electrodes 158 that encased in an electrode casing 170. The electrode casing 170 may be formed of highly durable bio-compatible materials, such as silicone or PDMS. In the paddle-type lead 173 illustrated in FIG. 8C, the rectifier and filter component 134, the voltage regulator component 136, and the internal stimulator communications processor 138 may be contained in a housing 172 that is adjacent to the paddle-type lead 173. The resonator component 130 and the pickup component 132 may be displaced a short distance from the paddle-type lead and connected to the circuitry with a lead wire.

Figure 8D:
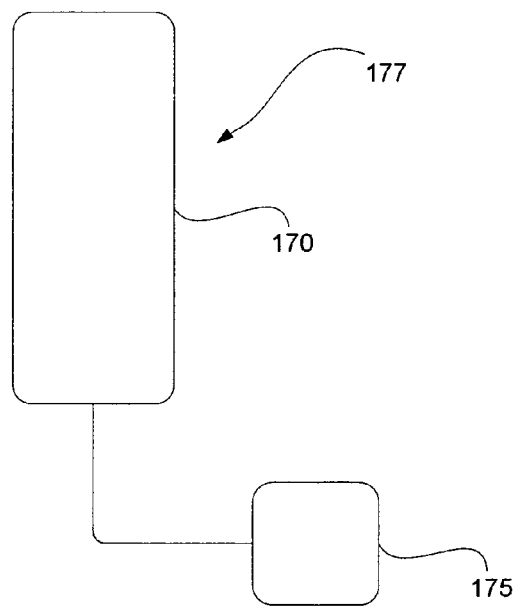

FIG. 8D illustrates another example of an internal stimulator 106 in which the paddle-type lead 177 is displaced a short distance from a housing 175 that contains the resonant component 130, the pickup component 132, the voltage regulator component 136, and the internal stimulator communications processor 138. The paddle-type lead 177 illustrated in FIG. 8D lead may include an array of stimulus electrodes 158 that encased in an electrode casing 170. The electrode casing 170 may be formed of highly durable bio-compatible materials, such as silicone or PDMS. In the paddle-type lead 177 illustrated in FIG. 8D, the rectifier and filter component 134, the voltage regulator component 136, and the internal stimulator communications processor 138, resonator component 130 and pickup component 132 may be displaced in a housing 175 a short distance from the paddle-type lead 177 and connected to the paddle-type lead with a lead wire.

Figure 9A:
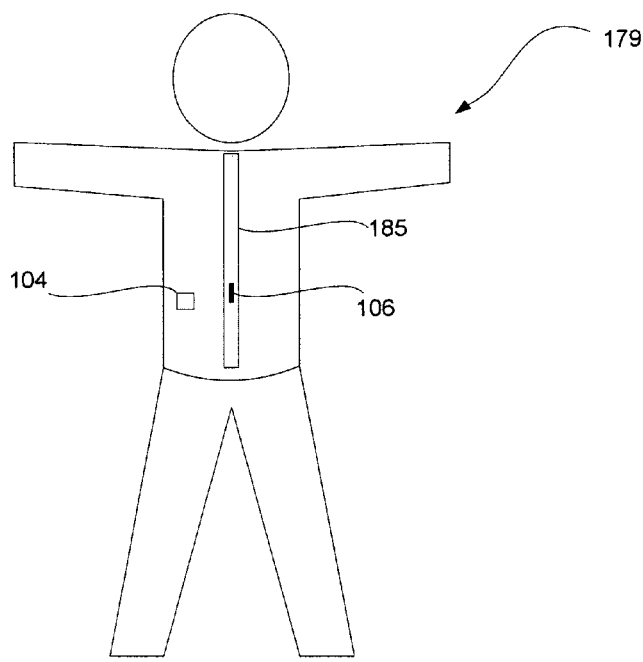
FIG. 9A illustrates a coronal cross-section of the human body.
Figure 9B:
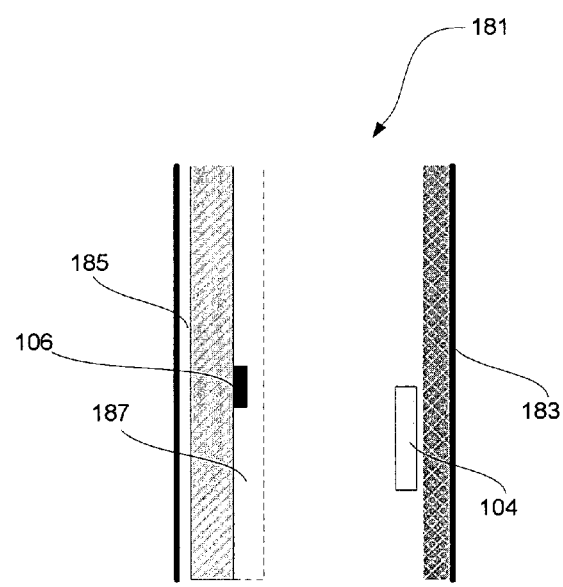
FIG. 9B illustrates an enlarged sagittal cross-section of a portion of the posterior region of a human body.

As described above, the system and method described herein may be used as a spinal cord stimulator to provide stimulation to the spinal cord of a patient. FIGS. 9A-9B illustrate the location of the internal controller 104 and internal stimulator 106 used for spinal cord stimulation in the human body 179. FIG. 9A illustrates a coronal cross-section and FIG. 9B illustrates an enlarged sagittal cross-section of a portion of the posterior region 181 of a human body 179 showing the internal controller 104 and internal stimulator 106. Preferably, the internal controller 104 is placed under the skin 183, and looking into the coronal plane, may lie in either half of the body, the axis being the spinal column 185 (refer to FIG. 9A). The internal stimulator 106 may be in the epidural space 187, either as percutaneous leads, as a paddle-type lead (as illustrated in FIGS. 8A-8D), or as any other type of stimulating mechanism, as described herein. In case of paddle-type lead, the paddle may conform to the geometry of the dura, and may be fed by a lead. The lead (for paddles), leads (for percutaneous electrodes), and leads of any other type of stimulating mechanism may originate at the resonator component 130.

In order to efficiently harness power from the magnetic fields generated by the resonator component 122 in the internal controller 104, it is preferred that the resonator 130 at the internal stimulator have low loss, high inductance and be matched to the subsequent circuit elements in the internal stimulator 104, such as the rectifier and filter component 134, the voltage regulator 136, the internal stimulator communications processor 138 and the load component 140. The voltage induced in the resonator component 130 may be approximated based on the resonant frequency ($\omega$), the permeability of the medium ($\mu$), the area of the loop of the Antenna (A), the magnetic field strength (H), and the number of turns of the loop (N) according to the following equation:

$$V_{induced} = \omega \cdot \mu \cdot A \cdot H \cdot N$$

If the impedance looking into the resonator component 130 is considered to be $Z_A$, the current induced in the resonator component 130 may be approximated based on the resonant frequency ($\omega$), the permeability of the medium ($\mu$), the area of the loop of the Antenna (A), the magnetic field strength (H), the number of turns of the loop (N), and the impedance ($Z_A$) according to the following equation:

$$I_{induced} = \frac{\omega \cdot \mu \cdot A \cdot H \cdot N}{Z_A}$$

As a result, the maximum power that may be harnessed at the resonator component 130 may be approximated according to the following equation:

$$P_{harnessed} = \frac{(\omega \cdot \mu \cdot A \cdot H \cdot N)^2}{Z_A}$$

As noted above, the present system and method may be used to transfer power is in the near-field. When transferring power in near-fields, it is preferred that the distance between the resonant component 122 in the internal controller 104 and the resonant controller 130 in the internal stimulator be within the near-field region at the operating frequency. The appropriate wavelength of the electromagnetic field ($\lambda_{Effective}$) used in the system is based on the distance (D) between the two resonant components 122, 130 according to the following equation:

$$D < \frac{\lambda_{Effective}}{2\pi}$$

From the equations described above, it is seen that the amount of power harnessed at the resonant component 130 is based, in part, on the frequency of operation.

Figure 10:
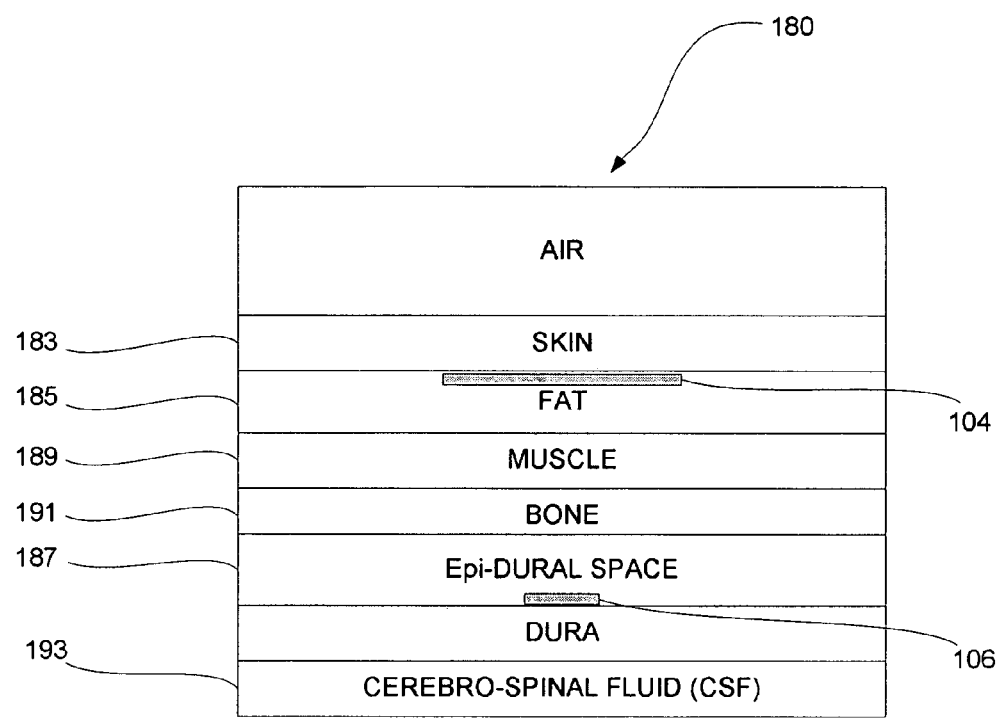
FIG. 10 illustrates an example of a simplified layered tissue model from the posterior region of the human body.

The frequency of operation may be chosen based on various factors, such as environmental conditions and maximum distance of efficient operation. FIG. 10A illustrates a simplified layered tissue model 180 from the posterior region 181 of the human body 179. It is noted that the tissue model illustrated in FIG. 10 is an approximation to characterize the medium and is not to scale. As noted above, it is preferred that the internal controller 104 be placed just under the skin 183, in the fat 185, and that the stimulating electrodes 158 of the internal stimulator 106 be placed in the epidural space 187. The tissue regions between internal controller 104 and the internal stimulator include a portion of the fat region 185, the muscle region 189, and the bone region 191. These regions will affect the field distribution and the efficiency of the energy transfer between the resonant component 122 and the resonant component 130. In addition, the proximity of the conductive CSF region 193 will also affect the characteristics of the field distribution. Given these environmental conditions, it is preferred that the distance between the resonant component 122 and the resonant component 130 is less than 4.5 inches. The frequency of operation in the present example may be approximately between 135 KHz and 150 KHz or, in the alternative, be between 2 MHz and 30 MHz. It is understood that frequency of operation may be between 150 KHz and 2 MHz or greater than 30 MHz.

Figure 11:
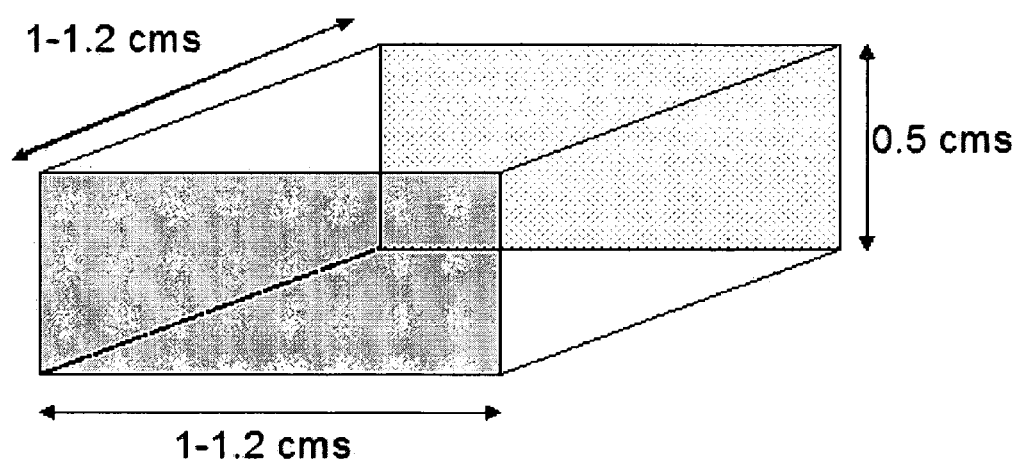
FIG. 11 is an illustration of an example of the total volume available to package a resonant component.

The resonator component 130 may be designed to be housed in a package that is suitable for being implanted in a human body. One example of a package designed to be implanted in a human body is illustrated in FIG. 11. As illustrated in FIG. 11, the package 192 designed to house the resonator component 130 may have a volume of approximately 0.8-1 cms by 0.8-1 cm by 0.3 cms. The package 192 for the resonant component 130 may also include approximately a 1 mm boundary on each side. Thus, in this example, the total volume available to package the resonant component 130 is 1-1.2 cms by 1-1.2 cms by 0.5 cms. It is understood that a greater volume may be used to house the resonator component 130 without departing from the teachings of the present example.

It is preferred that the available volume be utilized to maximize the quality factor of each of the resonant components 122, 130. Preferably, the quality factor of each resonant component 122, 130 is greater than 100. A quality factor of greater than 100 may be achieved based on the configuration and materials used to design the resonant component.

The configuration of the resonant components 122, 130 may be a squircle, a square, circular, rectangular or triangular planar spiral; a square, circular, rectangular, or triangular planar figure-of-eight; a squircle, a square, circular, rectangular, or triangular solenoid figure-of-eight; or a squircle, square, circular, rectangular, or triangular multi-layer solenoid. It is also contemplated that the resonant antennas 122, 130 may also be configured as two or more orthogonal antenna in any of the configurations described above. Other configurations known to those of ordinary skill may also be utilized.

Figure 12A:
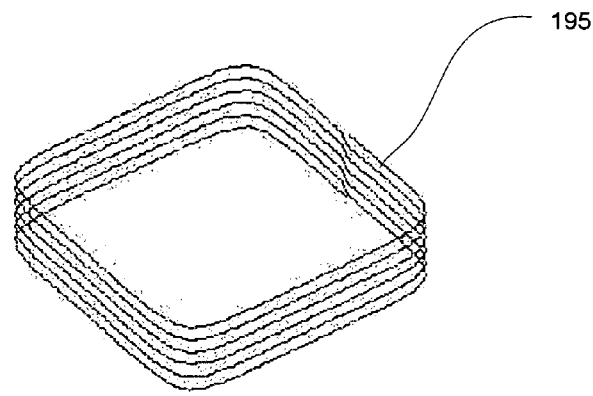
FIGS. 12A-12E illustrate examples of different resonant component configurations that may be designed to fit in the available volume illustrated in FIG. 11.
Figure 12B:
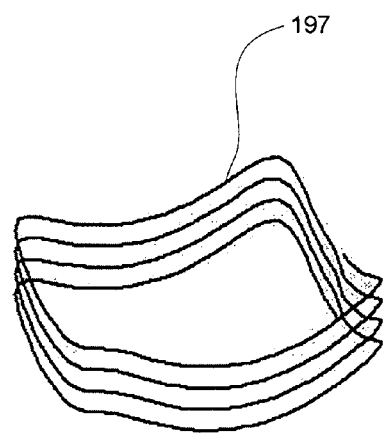
Figure 12C:
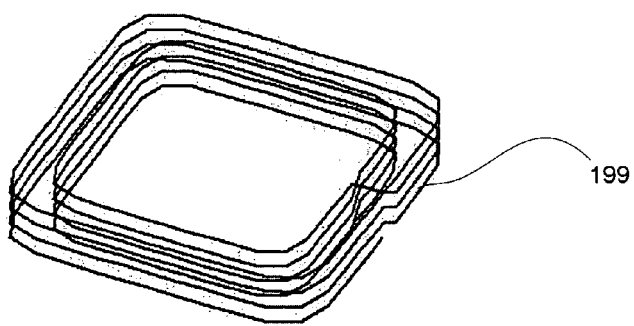
Figure 12D:
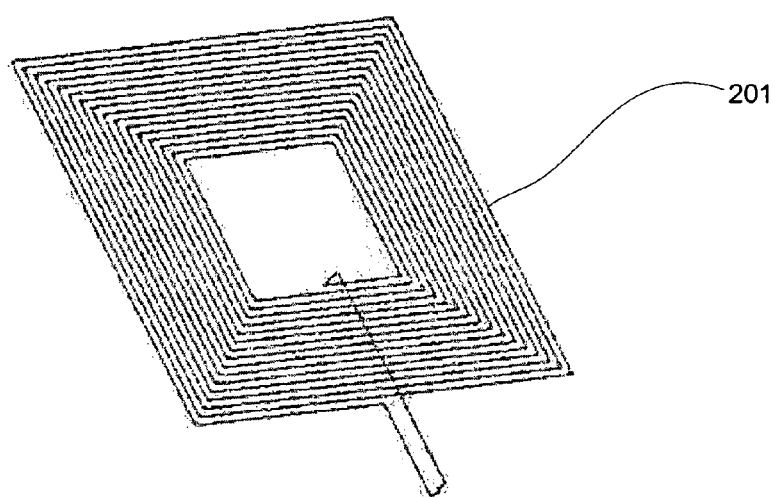
Figure 12E:
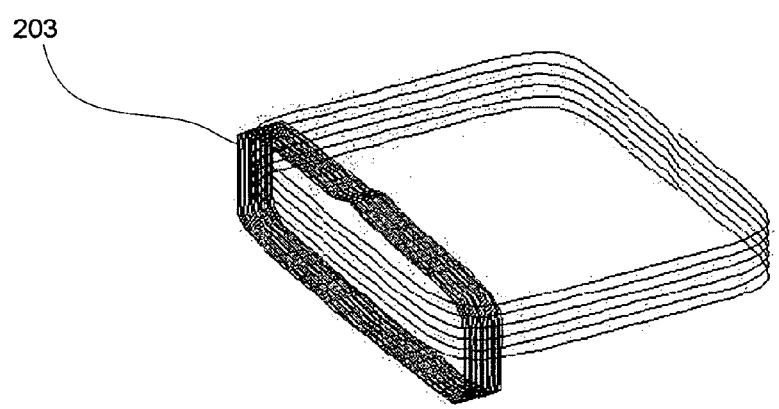

FIG. 12A-FIG. 12D illustrate examples of different resonant component configurations that may be designed to fit in the available volume. The resonant component structures illustrated in FIG. 12A-FIG. 12D may have conductors that are thin wire filaments but it is understood that wires may be of varying thicknesses, such as, for example between 1 μm and 3 mm. It is also understood that the cross-section could be one of a plurality of shapes known to those of ordinary skill in the art, such as, for example, circular, rectangular, or triangular. FIG. 12A illustrates a resonant component in a solenoid configuration 195. FIG. 12B illustrates a resonant component in a conformal solenoid configuration 197. The resonant component in a conformal solenoid configuration may take the form of a circular solenoid or a circular or rectangular spiral. FIG. 12C illustrates a resonant component in a multi-layer solenoid configuration 199. Although only two layers are illustrated in FIG. 12C, it is understood that any number of layers may be used. FIG. 12D illustrates a resonant component in a square spiral configuration 201. It is understood that other spiral configurations, such as a rectangular or square shape may be utilized. FIG. 12E illustrates a resonant component having an orthogonally oriented coil configuration 203. In such a configuration, one or more coils are orthogonally oriented. The coils may take any of the shapes described in FIGS. 12A-12D. The orthogonally oriented configuration may be used to reduce the dependence of the induced voltage on the orientation of the resonator components 122, 130. It is understood that the resonant components described herein may be self-resonant or be resonant by the addition of capacitive and/or inductive elements.

As described above, the cross-sectional shape of the wire that is used to form the resonant component 122, 130 may be circular, square, rectangular, or triangular. Preferably, the wire has a relatively small diameter, or height relative to the width of the wire, and may be on the order of twice the skin-depth at the operating frequency. FIG. 13A-FIG. 13 F illustrate cross-sections of wires that may be used in the design of the resonant component 122, 130. FIG. 13A illustrates a wire having a circular cross section 205. FIG. 13B illustrates a wire having a rectangular cross section in the form of a square 207. FIG. 13C illustrates a wire having a thin rectangular cross section 209. FIG. 13D illustrates a wire having an elliptical cross section 211. FIG. 13E illustrates a cross section of a litz wire 213. FIG. 13F illustrates a cross section of a copper tube 215. The wire may be copper, gold, silver-coated copper, silver-coated gold, or any other conductor.

It may be preferable to use a wire having a thin rectangular cross section, a wire having an elliptical cross section, a litz wire, or a copper tube for applications in which the frequency is greater than 100 kHz. For low volume application, it may be desirable to use a wire having a thin rectangular cross section, a wire having an elliptical cross section, a litz wire.

Figure 14A:
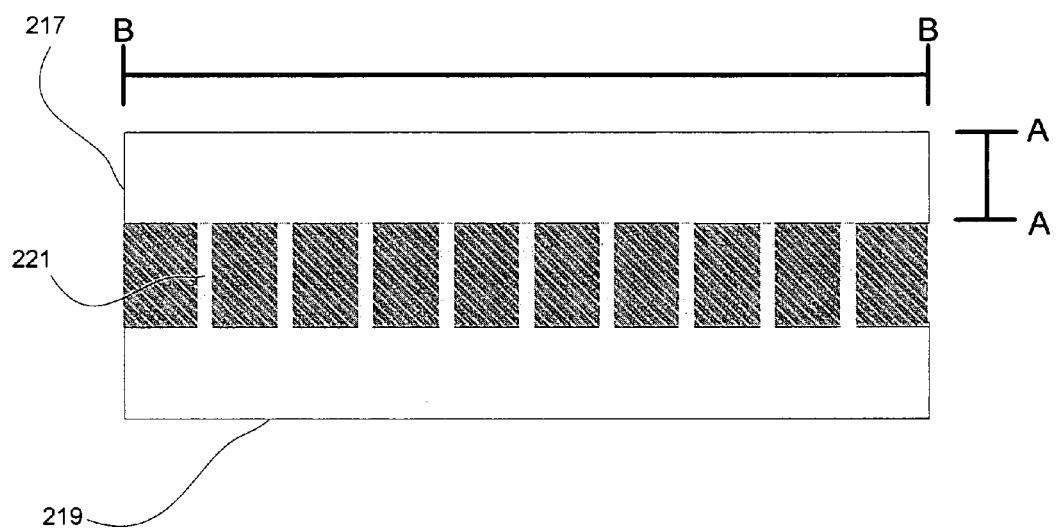
FIG. 14A illustrates a cross-section of one example of a resonant component; and, FIGS. 14B-14C illustrate examples of resonant component configurations.

The quality factor of the resonant component 122, 130 is based, in part, on the number of layers and the metal thickness and metal strip width of the wire in each layer. Each layer may be a single strip of metal having a metal thickness and metal strip width. FIG. 14A illustrates cross-section of a resonant component having a first layer 217 and a second layer 219. An insulating material 223 separates the first layer 217 from the second layer 219. The first layer 217 and second layer 219 are connected with vias 221 which traverse the insulating material 223. The metal thickness of the first layer 217 is identified by line A-A and the metal strip width of the first layer 219 is identified by line B-B. In one example, the metal thickness of a layer may be approximately twice the skin-depth. Each layer in a turn will have substantially the same metal thickness and metal strip width. A higher quality factor may be achieved using multiple layers for a single turn of coil. If additional layers are added to a turn of the coil, the additional layers include insulating material and are electrically connected to the other layers in that turn using vias through the insulating material. It is understood that by varying the number of turns, the metal thickness, and metal strip width, a higher quality factor may be achieved.

Figure 14B:
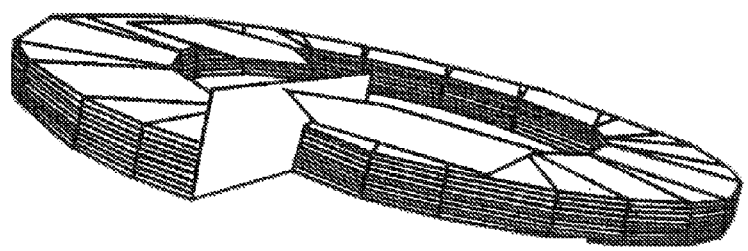

In one example, the resonant component 122, 130 may be a single turn coil having multiple layers, as illustrated in FIG. 14B. The single turn coil includes a single turn and may include a metal thickness of approximately 0.03 mm, a metal strip width of approximately 1.75 mm, and an outer radius of approximately 5 mm. The coil may have between 10 and 60 layers; however it is understood that the coil may have less than 10 or more than 60 layers in order to achieve a high quality factor. For example, for a five layer single turn coil having a metal thickness of 30 μm and a metal strip width of 1.75 mm, the quality factor at 27 MHz is approximately 242. Increasing the number of layers from five to twenty and keeping a metal thickness of 30 μm and a metal strip width of 1.75 mm, the quality factor is increased to approximately 400. It is also understood that metal strip width may be increased to achieve a higher quality factor.

Figure 14C:
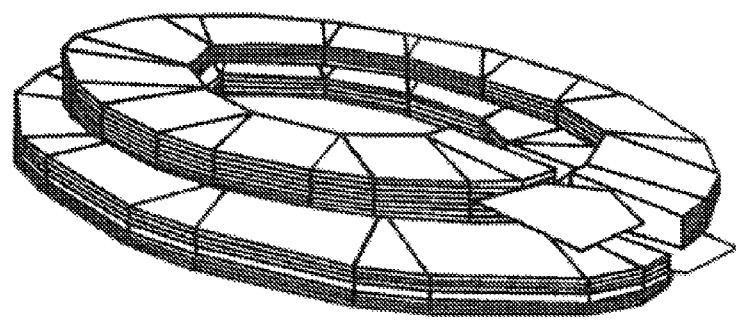

In another example, the resonant component 122, 130 may be coil having multiple turns and multiple layers, as illustrated in FIG. 14C. The coil may include two turns and may include a metal thickness of approximately 30 μm, a metal strip width of approximately 1.75 mm, and an outer coil radius of approximately 5 mm. Although the illustrated coil includes two turns, it is understood that the coil may include more than two turns. The coil preferably has between 10 and 60 layers; however it is understood that the coil may have less than 10 or more than 60 layers in order to achieve a higher quality factor. For example, for a ten layer two turn coil having a metal thickness of 30 μm and a metal strip width of 1.75 mm, the quality factor at 27 MHz is approximately 740. It is understood that metal strip width may be increased to achieve a higher quality factor.

It is also contemplated that other designs may be used for the resonator components 122, 130. For example, the designs shown in FIGS. 14B and 14C may be modified by using a thinner metal strip thickness, such as for example, approximately 50 μM. The metal thickness may be approximately 30 μm and the outer coil radius may be approximately 5 mm. Preferably, the coil has 15 layers, however it is understood that the coil may have more layers in order to achieve a high quality factor. It is also understood that the number of turns may be increased or decreased in order to achieve a high quality factor.

In order for the resonant component 122, 130 to be efficient at the operating frequency, it is preferred that the resonant component 122, 130 be resonant. The resonant component 122, 130 may be made resonant with the addition of a capacitor. The added capacitor may be a high quality factor capacitor. The rectifier and filter component 134, voltage regulator 136, internal stimulator communications processor 138, and load component 140 comprise electronics and active and passive circuits that are powered by the inductively coupled link between the resonant component 122 and the resonant component 130, as described above. In order to achieve maximum power transfer, it is preferred that the resonant component 130 be conjugate matched to the rectifier and filter component 134, voltage regulator 136, internal stimulator communications processor 138, and load component 140.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

What is claimed is:

1. A resonator for use in a system for energy transfer between a first device and a second device, the resonator comprising:
a coil having an operating frequency, the coil having a plurality of layers, each layer of the plurality of layers comprises a first conductor layer and a second conductor layer, an insulator positioned between the first and second conductor layers, and each layer in the plurality of layers having at least one turn wherein at least the first and second conductor layers are electrically connected, wherein the at least one turn comprises a plurality of layers, wherein each of the plurality of layers is substantially flat.

2. The resonator of claim 1 wherein each layer in the plurality of layers is electrically connected using at least one via.

3. The resonator of claim 1 wherein at least one conductor layer includes a thickness substantially equal to twice the skin-depth at the operating frequency.

4. The resonator of claim 1 wherein each of the plurality of layers of the at least one turn comprises a first conductor layer, a second conductor layer and an insulator positioned between the first and second conductor layers that are electrically connected using at least one via, and wherein the first or second conductor layers include a thickness substantially equal to twice the skin-depth at the operating frequency.

5. The resonator of claim 1 wherein the resonator has a quality factor greater than 100.

* * * * *